United States Patent
Metcalf

(10) Patent No.: US 12,409,152 B2
(45) Date of Patent: Sep. 9, 2025

(54) COMPOSITIONS AND METHODS RELATED TO DISSOLVED OXIDES

(71) Applicant: Natural Extraction Systems, LLC, Boulder, CO (US)

(72) Inventor: Douglas G. Metcalf, Boulder, CO (US)

(73) Assignee: Natural Extraction Systems, LLC, Boulder, CO (US)

( * ) Notice: Subject to any disclaimer, the term of this patent is extended or adjusted under 35 U.S.C. 154(b) by 778 days.

(21) Appl. No.: 17/639,280

(22) PCT Filed: Aug. 28, 2020

(86) PCT No.: PCT/US2020/048650
§ 371 (c)(1),
(2) Date: Feb. 28, 2022

(87) PCT Pub. No.: WO2021/042001
PCT Pub. Date: Mar. 4, 2021

(65) Prior Publication Data
US 2022/0362169 A1    Nov. 17, 2022

Related U.S. Application Data

(60) Provisional application No. 63/003,750, filed on Apr. 1, 2020, provisional application No. 62/969,612, filed on Feb. 3, 2020, provisional application No. 62/950,813, filed on Dec. 19, 2019, provisional application No. 62/935,488, filed on Nov. 14, 2019, provisional application No. 62/928,954, filed on Oct. 31, 2019, provisional application No. 62/923,411, filed on Oct. 18, 2019, provisional application No. 62/894,455, filed on Aug. 30, 2019.

(51) Int. Cl.
*A61K 31/05* (2006.01)
*A61K 33/24* (2019.01)

(52) U.S. Cl.
CPC .............. *A61K 31/05* (2013.01); *A61K 33/24* (2013.01)

(58) Field of Classification Search
CPC ...... A61K 31/05; A61K 33/24; A61K 31/085; A61K 31/12; A61K 31/352; A61K 31/353; A61K 9/0014; A61K 9/0053; A61K 47/10; A61K 47/26; A61K 9/0095; A61P 25/00; C07C 39/235; C07C 39/23; C07C 39/21
See application file for complete search history.

(56) References Cited

U.S. PATENT DOCUMENTS

2010/0273895 A1* 10/2010 Stinchcomb ............ A61P 19/02
514/733

* cited by examiner

*Primary Examiner* — Amanda L. Aguirre
(74) *Attorney, Agent, or Firm* — Douglas G. Metcalf

(57) ABSTRACT

Various aspects of this patent document relate to compositions that comprise an anion that is the conjugate base of a hydrophobic molecule that has a pKa, for example, of at least 7 and no greater than 12. These compositions display improved properties when formulated to interact with an organism because the anions carry negative charges that allows them to both dissolve in water-miscible liquids and maximize their surface area. Interaction with an organism results in at least partial conversion of the anion into the hydrophobic molecule after which the hydrophobic molecule partitions out of a water-miscible liquid and into the organism.

10 Claims, No Drawings

COMPOSITIONS AND METHODS RELATED TO DISSOLVED OXIDES

CROSS-REFERENCE TO RELATED APPLICATIONS

This patent document is the U.S. national stage under 35 U.S.C. § 371 of international application PCT/US20/48650, filed Aug. 28, 2020, which claims priority to U.S. Provisional Patent Application No. 62/894,455, filed Aug. 30, 2019; U.S. Provisional Patent Application No. 62/923,411, filed Oct. 18, 2019; U.S. Provisional Patent Application No. 62/928,954, filed Oct. 31, 2019; U.S. Provisional Patent Application No. 62/935,488, filed Nov. 14, 2019; U.S. Provisional Patent Application No. 62/950,813, filed Dec. 19, 2019; U.S. Provisional Patent Application No. 62/969,612, filed Feb. 3, 2020; and U.S. Provisional Patent Application No. 63/003,750, filed Apr. 1, 2020, each of which is incorporated by reference in its entirety.

BACKGROUND

Many hydrophobic bioactive molecules including high-value pharmaceuticals display poor bioavailability and pharmacokinetics. Formulations that improve the bioavailability and pharmacokinetics of hydrophobic bioactive molecules are desirable.

SUMMARY

Various aspects of this patent document relate to anions that are dissolved in water-miscible liquids and that convert into hydrophobic molecules at neutral pH. The anions carry net negative charges that repel each other to maximize their surface area. The administration of anions that are dissolved in a water-miscible liquid to an organism results in the pH-dependent conversion of the anions into hydrophobic molecules that are generally insoluble in water-miscible liquids and bodily fluids. The molecules then rapidly partition out of the water-miscible liquid and adhere to the epithelium where they absorb into the blood (during oral administration) or the skin and underlying tissue (during topical administration). Absorption through the epithelium of the mouth and throat avoids first-pass metabolism and improves both bioavailability and pharmacokinetics.

DETAILED DESCRIPTION

Various aspects of this patent document relate to a composition, comprising a liquid phase that comprises both an anion and a solvent, wherein: (1) the solvent is either water or an alcohol that has the formula $C_xH_yO_z$; all of the atoms of the alcohol are connected by single bonds; x is a positive integer; z is a positive integer that is no greater than x; and either (i) the alcohol is linear, and $y=2x+2$ or (ii) the alcohol contains a monocycle, and $y=2x$; (2) the anion is dissolved in the solvent; (3) the anion has a net charge of $-1$; (4) the anion has a conjugate acid that is a molecule; (5) the molecule has a net charge of zero; (6) the molecule has a solubility in water that is less than 10 grams per liter at a pH of 7; (7) the molecule comprises a hydroxyl group (—OH) that comprises an oxygen atom that is covalently bound to a carbon atom of an aromatic ring of the molecule by a single bond; (8) the anion comprises exactly one oxide group (—O$^-$), and the oxide group comprises an oxygen atom that is covalently bound to a carbon atom of an aromatic ring of the anion by a single bond; (9) the oxygen atom of the hydroxyl group of the molecule has a connectivity to other heavy atoms of the molecule; (10) the oxygen atom of the oxide group of the anion has a connectivity to other heavy atoms of the anion; and (11) the connectivity of the oxygen atom of the hydroxyl group of the molecule to other heavy atoms of the molecule is identical to the connectivity of the oxygen atom of the oxide group of the anion to other heavy atoms of the anion.

"Comprising" and "comprise(s)" refer to open sets such that a liquid phase that comprises both an anion and a solvent can also comprise, for example, a cosolvent.

"Dissolved" refers to a solute that is solvated in a liquid phase by either (i) a solvent, (ii) a cosolvent, or (iii) both a solvent and a cosolvent; a chemical species that is present within a phase that is dispersed within a liquid phase, such as the dispersed phase of an emulsion, is not dissolved in the liquid phase; a chemical species that is non-covalently bound to any chemical species that is a solid in the absence of a solvent, such as a cyclodextrin, is not dissolved in a solvent.

"Aromatic ring," as used in this patent document, refers to a cycle of atoms comprising at least 3 carbon atoms, in which each carbon atom of the cycle is an unsaturated carbon atom.

"Unsaturated carbon atom" refers to a carbon atom that is directly bound to less than 4 other atoms.

"Connectivity" refers to the covalent bonds that connect atoms within a chemical species independent of whether any given covalent bond can be characterized as a single, double, or triple bond.

"Heavy atom" refers to an atom of any element other than hydrogen.

In some embodiments, the alcohol is methanol, ethanol, 2-propanol, propane-1,2-diol, propane-1,3-diol, propane-1,2,3-triol, butane-1,3-diol, butane-1,4-diol, erythritol, threitol, arabitol, xylitol, ribitol, mannitol, sorbitol, galactitol, fucitol, iditol, inositol, volemitol, or polyethylene glycol. In some embodiments, x is at least 2 and no greater than 7; y is at least 1 and no greater than 7; and H is at least 6 and no greater than 16. In some specific embodiments, the alcohol is ethanol, propane-1,2-diol, propane-1,3-diol, propane-1,2,3-triol, erythritol, xylitol, or sorbitol. In some very specific embodiments, the alcohol is ethanol or propane-1,2,3-triol.

In some specific embodiments, the solvent is water. In some specific embodiments, the solvent is ethanol. In some specific embodiments, the solvent is propane-1,2,3-triol.

In some embodiments, the molecule has a solubility in water that is less than 1 gram per liter at a pH of 7. In some specific embodiments, the molecule has a solubility in water that is less than 100 milligrams per liter at a pH of 7. In some even more specific embodiments, the molecule has a solubility in water that is less than 10 milligrams per liter at a pH of 7. In some very specific embodiments, the molecule has a solubility in water that is less than 1 milligram per liter at a pH of 7. Solubility is determined at 20 degrees Celsius in deionized water.

In some embodiments, the composition comprises the solvent at a concentration of at least 50 percent by mass. In some specific embodiments, the composition comprises the solvent at a concentration of at least 60 percent by mass. In some very specific embodiments, the composition comprises the solvent at a concentration of at least 60 percent no greater than 95 percent by mass.

In some embodiments, the solvent is ethanol, propane-1,2-diol, propane-1,3-diol, or propane-1,2,3-triol. In some specific embodiments, the composition comprises ethanol, and the solvent is water, propane-1,2-diol, propane-1,3-diol, or propane-1,2,3-triol. In some specific embodiments, the composition comprises water, and the solvent is ethanol, propane-1,2-diol, propane-1,3-diol, or propane-1,2,3-triol. In some very specific embodiments, the composition comprises ethanol and water, and the solvent is propane-1,2-diol, propane-1,3-diol, or propane-1,2,3-triol.

In some embodiments, the composition comprises a cation. In some specific embodiments, the composition comprises the cation and the anion at a molar ratio of at least 1:1 and no greater than 5:4.

In some embodiments, the composition comprises a concentration of the anion that is dissolved in the solvent, wherein the molecule has a solubility in the liquid phase at a neutral pH that is less than the concentration of the anion that is dissolved in the solvent. In some specific embodiments, the molecule has a solubility in the liquid phase at a neutral pH that is less than 10 percent of the concentration of the anion that is dissolved in the solvent. In some very specific embodiments, the molecule has a solubility in the liquid phase at a neutral pH that is less than 1 percent of the concentration of the anion that is dissolved in the solvent. "Solubility" refers to the ability of a chemical species (for example, a molecule) to dissolve in a solvent as the same chemical species (the molecule) and does not refer to the ability of a chemical species (for example, a molecule) to dissolve in a solvent as a different chemical species (for example, as an anion); the empirical measurement of "solubility" may require—but does not necessarily require—a composition or liquid phase that has a lower pH than the compositions and liquid phases disclosed and claimed in this patent document, but that is otherwise identical to the compositions and liquid phases disclosed and claimed in this patent document. "Neutral pH" refers to the pH at which the conjugate acid of a solvent and the conjugate base of the solvent are present at equal concentrations.

In some embodiments, the composition comprises the molecule and the anion at a molar ratio of at least 1:1,000,000 and less than 10:1. In some specific embodiments, the composition comprises the molecule and the anion at a molar ratio of at least 1:1,000,000 and less than 1:1. In some very specific embodiments, the composition comprises the molecule and the anion at a molar ratio of at least 1:1000 and no greater than 9:10.

In some embodiments, the composition comprises the anion at a concentration of at least 1 gram per liter. In some specific embodiments, the composition comprises the anion at a concentration of at least 10 grams per liter. In some very specific embodiments, the composition comprises the anion at a concentration of at least 100 grams per liter.

Various aspects of this patent document relate to a composition comprising a solid phase that comprises a salt that comprises both an anion and a cation, wherein: (1) the anion has a net charge of −1; (2) the anion has a conjugate acid that is a molecule; (3) the molecule has a net charge of zero; (4) the molecule comprises a hydroxyl group that comprises an oxygen atom that is covalently bound to a carbon atom of an aromatic ring of the molecule by a single bond; (5) the anion comprises exactly one oxide group, and the oxide group comprises an oxygen atom that is covalently bound to a carbon atom of an aromatic ring of the anion by a single bond; (6) the oxygen atom of the hydroxyl group of the molecule has a connectivity to other heavy atoms of the molecule; (7) the oxygen atom of the oxide group of the anion has a connectivity to other heavy atoms of the anion; (8) the connectivity of the oxygen atom of the hydroxyl group of the molecule to other heavy atoms of the molecule is identical to the connectivity of the oxygen atom of the oxide group of the anion to other heavy atoms of the anion; and (9) the salt comprises the anion and the cation at a molar ratio of either 1:1, 2:1, or 3:1.

In some embodiments, the cation of a liquid phase or a solid phase is either a metal cation or an ammonium cation. In some specific embodiments, the cation is either sodium cation ("Na+"); potassium cation ("K+"); magnesium cation ("Mg++"); calcium cation ("Ca++"); zinc cation ("Zn++"); manganese cation ("Mn++"); iron (II) cation ("Fe++"); iron (III) cation ("Fe+++"); copper (I) cation ("Cu+"); copper (II) cation ("Cu++"); ammonium ("NH4+"); protonated ethanolamine; choline; protonated sphingosine; protonated lysine; or protonated arginine. In some very specific embodiments, the cation is sodium cation. In some very specific embodiments, the cation is potassium cation.

In some embodiments, the molecule has a pKa in water that is greater than 6. In some specific embodiments, the molecule has a pKa in water that is greater than 6.5. In some even more specific embodiments, the molecule has a pKa in water that is greater than 7. In some very specific embodiments, the molecule has a pKa in water that is greater than 7.5.

"pKa" refers to the negative logarithm-base-10 of an acid dissociation constant.

In some embodiments, the molecule has a pKa in water that is less than 14. In some specific embodiments, the molecule has a pKa in water that is less than 13. In some very specific embodiments, the molecule has a pKa in water that is less than 12.

In some embodiments, the anion has a general formula I, II, III, IV, V, VI, VII, VIII, IX, X, XI, XII, XIII, XIV, XV, XVI, XVII, XVIII, XIX, XX, XXI, XXII, XXIII, XXIV, XXV, XXVI, XXVII, XXVIII, XXIX, XXX, XXXI, XXXII, XXXIII, XXXIV, XXXV, XXXVI, XXXVII, XXXVIII, XXXIX, XL, XLI, XLII, XLIII, XLIV, XLV, XLVI, XLVII, XLVIII, XLIX, L, LI, LII, LIII, LIV, LV, or LVI, each of which is depicted below.

In some embodiments, each skeletal atom in the preceding general formulas is a carbon atom except that each asterisk (*) depicts an independent, optional substitution of a skeletal atom with either an oxygen atom, a sulfur atom, a sulfinyl (—S(═O)—), a sulfonyl (—S(═O)$_2$—), or a nitrogen atom.

In some specific embodiments, each skeletal atom is a carbon atom except that 1, 2, 3, or 4 skeletal atoms that are marked with an asterisk (*) are substituted with an oxygen atom, a sulfur atom, or a nitrogen atom. In some very specific embodiments, each skeletal atom is a carbon atom except that 1 or 2 skeletal atoms that are marked with an asterisk (*) are substituted with an oxygen atom. "Skeletal atom" refers to each intersection of lines in a general formula, which depict the position of an atom.

In some embodiments, each skeletal atom is a carbon atom.

In some embodiments, each cross (†) in the general formulas depicts an optional R group, which occurs for each odd-numbered R group that is bonded to a skeletal atom that is either a carbon atom or a nitrogen atom; which is omitted for each odd-numbered R group that is bonded to an oxygen atom, a sulfur atom, a sulfinyl, or a sulfonyl; which occurs for each even-numbered R group that is bonded to a skeletal atom that is a saturated carbon atom; and which is omitted for each even-numbered R group that is bonded to a skeletal atom that is an unsaturated carbon atom. Odd-numbered R groups comprise R1, R3, R5, R7, R9, R11, R21, R23, R25, R27, R29, R31, R32, R35,

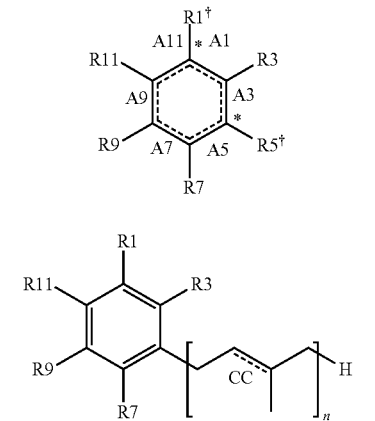
I
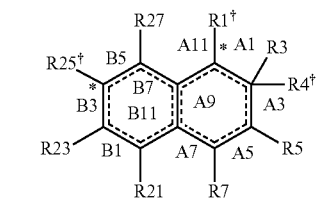
II
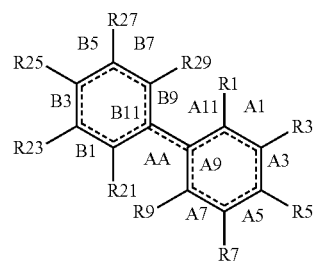
III
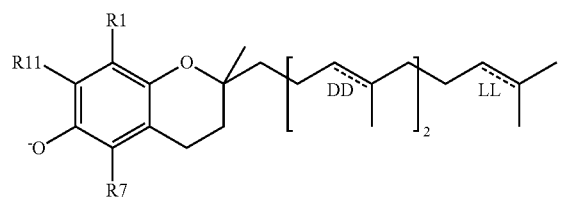
IV
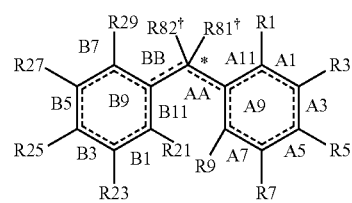
V
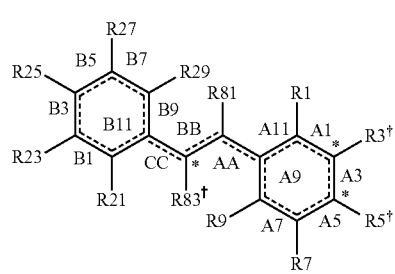
VI
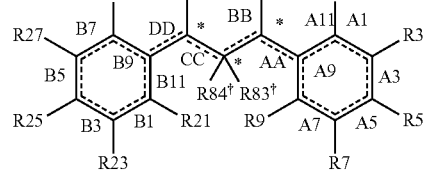
VIII
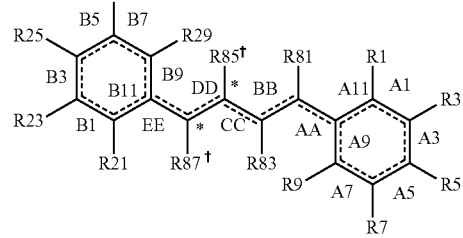
IX
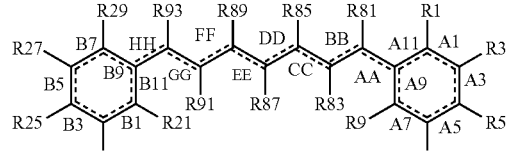
X
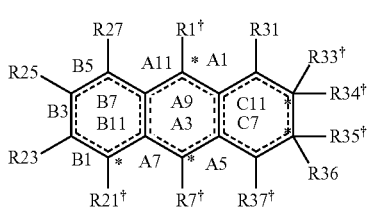
XI
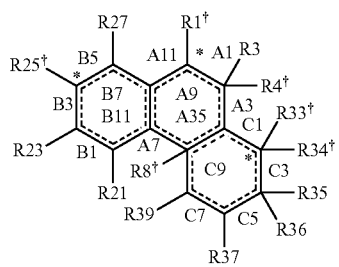
XII
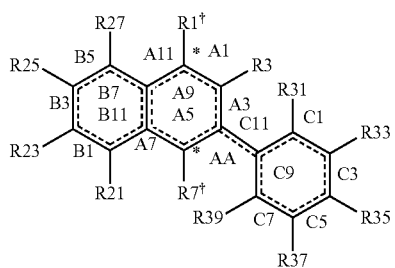
XIII XIV
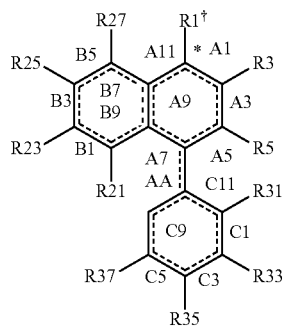
XV
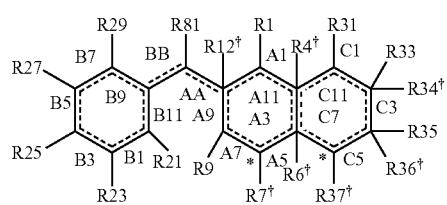
XVI
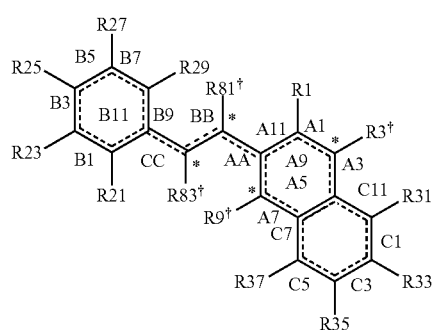
XVII
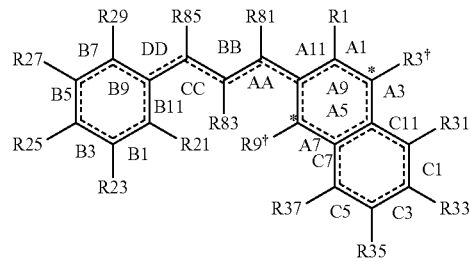
XVIII
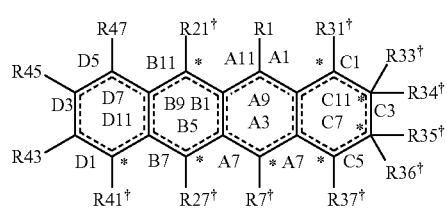
XIX
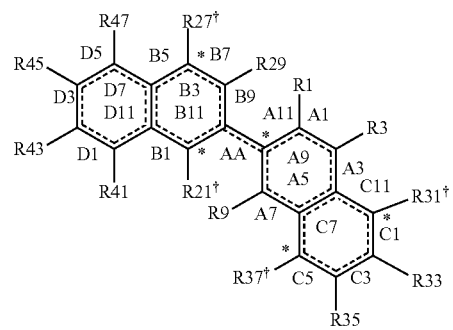
XX
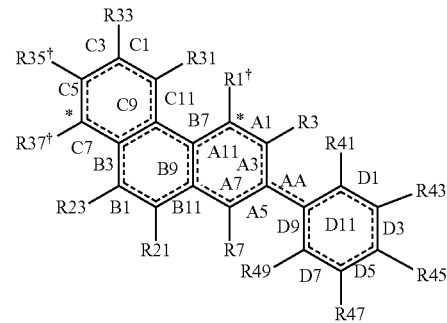
XXI
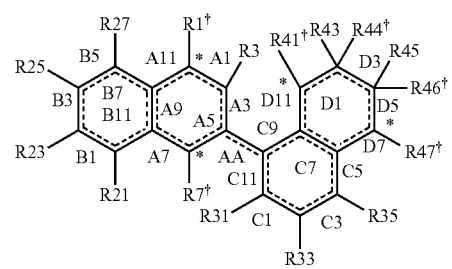
XXII
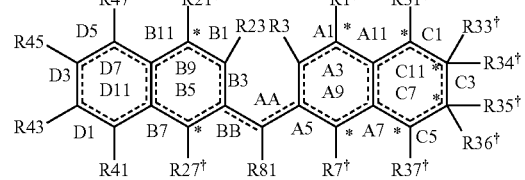
XXIII
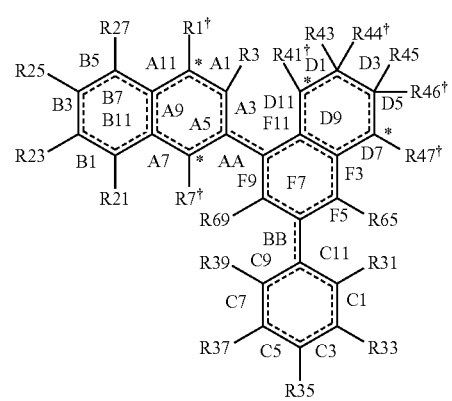

-continued

XXIV

XXV

XXVI

XXVII

XXVIII

XXIX

XXX

XXXI

XXXII

XXXIII

XXXIV

XXXV

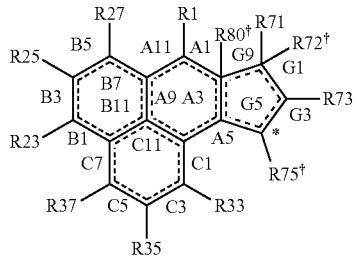
XXXVI
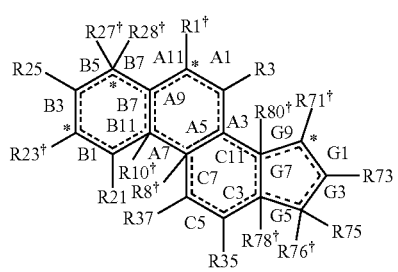
XXXVII
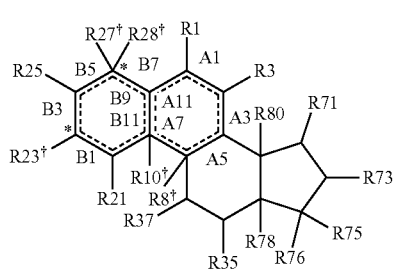
XXXVIII
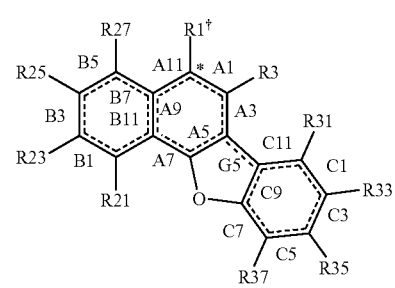
XXXIX
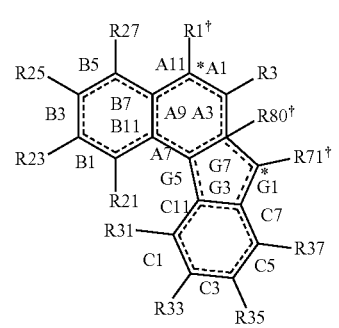
XL
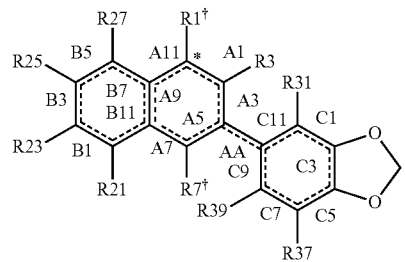
XLII
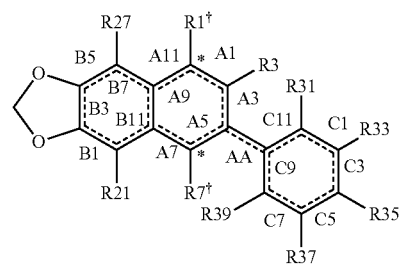
XLI
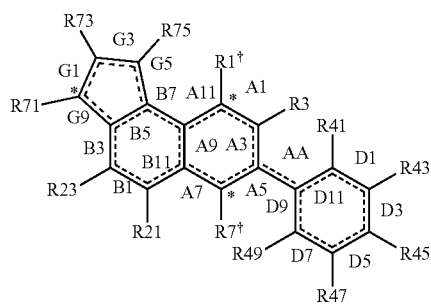
XLIV
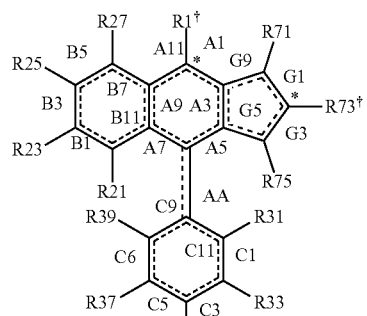
XLIII
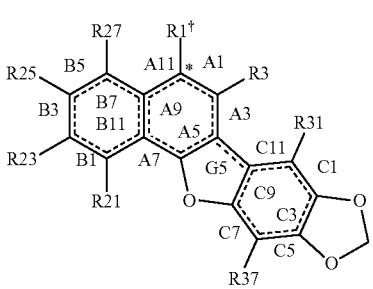
XLVI -continued
XLV
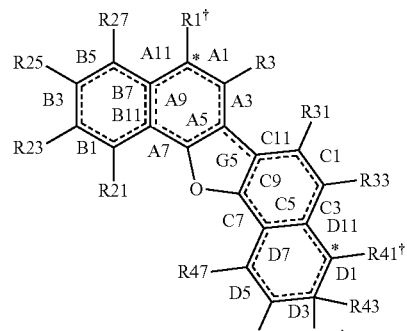
XLVIII
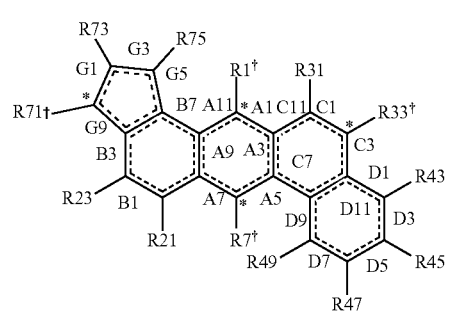
XLVII
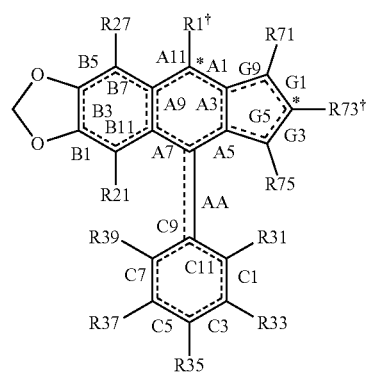
XLIX
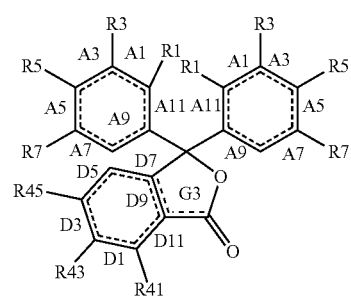
L
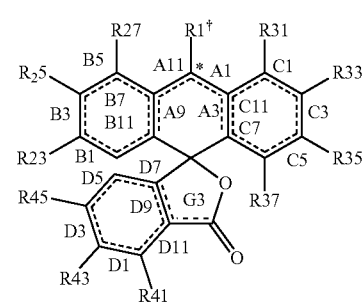
-continued
LI
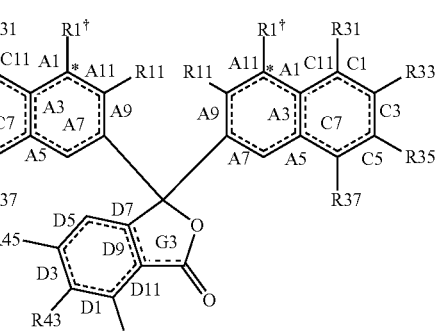
LII
LIII
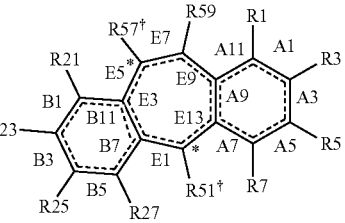
LIV
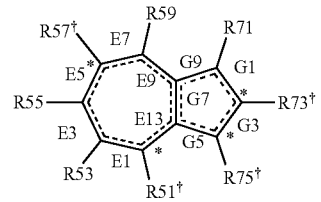
LV
LVII
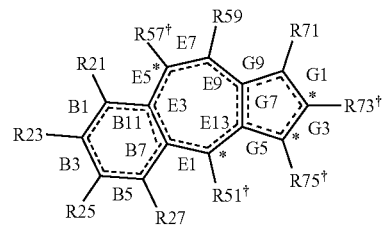

-continued

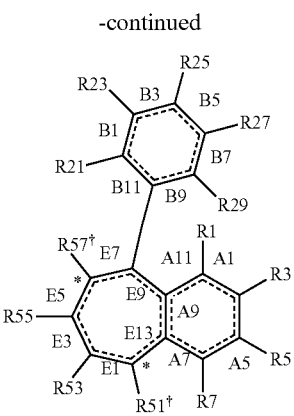

LVI

R37, R39, R41, R43, R45, R47, R49, R51, R53, R55, R57, R59, R61, R63, R65, R67, R69, R71, R73, R75, R77, R79, R81, R,83, R85, R87, R89, R91, and R93. Even-numbered R groups comprise R4, R6, R8, R10, R12, R28, R34, R36, R44, R46, R72, R76, R78, R80, R82, and R84.

"Saturated carbon atom" refers to a carbon atom that is directly bound to 4 other atoms.

In all embodiments, exactly one R group is oxide, and this R group is selected such that the oxide is covalently bound to a carbon atom of an aromatic ring by a single bond.

In all embodiments, each dotted line depicts an optional double bond. In the absence of a double bond, a dotted line is disregarded.

In some embodiments, the general formulas comprise one or more implicit hydrogen atoms. In some specific embodiments, an optional implicit hydrogen atom is bonded to each skeletal atom that is a carbon atom that is not bonded to an even-numbered R group. "Implicit hydrogen atom" refers to a hydrogen atom that is not depicted in a general formula, but that is necessarily bound to a skeletal atom that is a carbon atom such that the carbon atom is tetravalent.

In some embodiments, optional double bonds are selected and optional implicit hydrogen atoms are selected such that (i) the R group that is oxide is covalently bound to a carbon atom of an aromatic ring by a single bond, and (ii) no skeletal atom carries a full charge.

In some embodiments, each R group that occurs, other than the R group that is oxide, is independently selected from H; a halogen; hydroxy; amino; oxo; formyl; isocyano; carbamoyl; nitro; a substituted or unsubstituted C3-C10 cycloalkyl, aryl, arylalkyl, arylcarbonyl, arylcarbonyloxy, arlycarbonylamino, aryloxycarbonyl, arylcarbamoyl, arylalkylcarbonyl, arylalkylcarbonyloxy, arylalkylcarbonylamino, arylalkyloxycarbonyl, or arylalkylcarbamoyl; and a substituted or unsubstituted, straight or branched C1-C12 alkyl, alkylidene, alkyloxy, alkylsulfanyl, alkylamino, alkylcarbonyl, alkylcarbonyloxy, alkylcarbonylsulfanyl, alkylcarbonylamino, alkyloxycarbonyl, alkylsulfanylcarbonyl, or alkylcarbamoyl, wherein substituted refers to at least one of, in any order and without limitation, (i) the substitution of two hydrogen atoms with a double bond, (ii) the substitution of a double bond with two hydrogen atoms, (iii) the substitution of a hydrogen atom with a halogen; hydroxy; amino; formyl; isocyano; carbamoyl; nitro; a substituted or unsubstituted C3-C10 cycloalkyl, aryl, arylalkyl, arylcarbonyl, arylcarbonyloxy, arlycarbonylamino, aryloxycarbonyl, arylcarbamoyl, arylalkylcarbonyl, arylalkylcarbonyloxy, arylalkylcarbonylamino, arylalkyloxycarbonyl, or arylalkylcarbamoyl; or a substituted or unsubstituted, straight or branched C1-C12 alkyl, alkylidene, alkyloxy, alkylsulfanyl, alkylamino, alkylcarbonyl, alkylcarbonyloxy, alkylcarbonylsulfanyl, alkylcarbonylamino, alkyloxycarbonyl, alkylsulfanylcarbonyl, or alkylcarbamoyl, (iv) the substitution of two hydrogen atoms with methylene, epoxy, or a substituted or unsubstituted, straight or branched C1-C12 alkyl such that the substitution of the two hydrogen atoms forms a cycle that consists of 3 to 14 atoms, (v) the substitution of two hydrogen atoms with either oxo or a substituted or unsubstituted, straight or branched C1-C12 alkylidene, and (vi) the substitution of a methylene bridge (—CH$_2$—) with an oxygen atom, a sulfur atom, sulfinyl, sulfonyl, a protonated nitrogen atom, or a substituted or unsubstituted, straight or branched C1-C12 alkylamino, except that two R groups may be optionally co-selected from methylene, epoxy, or a substituted or unsubstituted, straight or branched C1-C12 alkyl such that the two R groups form cycle that consists of 3 to 14 atoms.

"Halogen" refers to any one of F, Cl, Br, and I.

"C3-C10 cycloalkyl" refers to any one of cyclopropyl, cyclobutyl, cyclopentyl, cyclohexyl, and cycloheptyl.

"C3-C10 aryl" refers to any one of furanyl, thienyl, pyrrolyl, phenyl, troponyl, benzofuranyl, benzothienyl, indolyl, isobenzofuranyl, benzo[c]thienyl, isoindolyl, and naphthyl, in which the aryl is bound to a parent chain (such as a general formula) by any heavy atom of the aryl.

"C3-C10 arylalkyl" refers to any C3-C10 aryl that is bound to any carbon atom of a branched or unbranched hydrocarbon chain by any heavy atom of the aryl, in which the hydrocarbon chain is bound to a parent chain by any carbon atom of the hydrocarbon chain, which is optionally the same carbon atom that is bound to the aryl; and the C3-C10 aryl and the alkyl contain a total of at least 3 and no greater than 10 carbon atoms.

"C3-C10 arylcarbonyl" refers to a C3-C10 aryl that is bound to a carbonyl carbon atom by any heavy atom of the aryl, in which the carbonyl carbon atom is bound to a parent chain, and in which the C3-C10 aryl and the carbonyl contain a total of at least 3 and no greater than 10 carbon atoms.

"C3-C10 arylcarbonyloxy" refers to a C3-C10 aryl that is bound to a carbonyl carbon atom by any heavy atom of the aryl, in which the carbonyl carbon atom is bound an oxygen atom other than its carbonyl oxygen atom; the oxygen atom is bound to a parent chain; and the C3-C10 aryl and the carbonyl contain a total of at least 3 and no greater than 10 carbon atoms.

"C3-C10 arlycarbonylamino" refers to a C3-C10 aryl that is bound to a carbonyl carbon atom by any heavy atom of the aryl, in which the carbonyl carbon atom is bound a protonated nitrogen atom; the protonated nitrogen atom is bound to a parent chain; and the C3-C10 aryl and the carbonyl contain a total of at least 3 and no greater than 10 carbon atoms.

"C3-C10 aryloxycarbonyl" refers to a C3-C10 aryl that is bound to an oxygen atom by any heavy atom of the aryl, in which the oxygen atom is bound a carbonyl carbon atom; the carbonyl carbon atom is bound to a parent chain; and the C3-C10 aryl and the carbonyl contain a total of at least 3 and no greater than 10 carbon atoms.

"C3-C10 arylcarbamoyl" refers to a C3-C10 aryl that is bound to a protonated nitrogen atom by any heavy atom of the aryl, in which the protonated nitrogen atom is bound a carbonyl carbon atom; the carbonyl carbon atom is bound to a parent chain; and the C3-C10 aryl and the carbonyl contain a total of at least 3 and no greater than 10 carbon atoms "C3-C10 arylalkylcarbonyl" refers to a C3-C10 aryl that is bound to any carbon atom of a branched or unbranched hydrocarbon chain by any heavy atom of the aryl, in which the hydrocarbon chain is bound to a carbonyl carbon atom by any carbon atom of the hydrocarbon chain, which is optionally the same carbon atom that is bound to the aryl; the carbonyl carbon atom is bound to a parent chain; and the C3-C10 aryl, the hydrocarbon chain, and the carbonyl contain a total of at least 3 and no greater than 10 carbon atoms.

"C3-C10 arylalkylcarbonyloxy" refers to a C3-C10 aryl that is bound to any carbon atom of a branched or unbranched hydrocarbon chain by any heavy atom of the aryl, in which the hydrocarbon chain is bound to a carbonyl carbon atom by any carbon atom of the hydrocarbon chain, which is optionally the same carbon atom that is bound to the aryl; the carbonyl carbon atom is bound to an oxygen atom other than its carbonyl oxygen atom; the oxygen atom is bound to a parent chain; and the C3-C10 aryl, the hydrocarbon chain, and the carbonyl contain a total of at least 3 and no greater than 10 carbon atoms.

"C3-C10 arylalkylcarbonylamino" refers to a C3-C10 aryl that is bound to any carbon atom of a branched or unbranched hydrocarbon chain by any heavy atom of the aryl, in which the hydrocarbon chain is bound to a carbonyl carbon atom by any carbon atom of the hydrocarbon chain, which is optionally the same carbon atom that is bound to the aryl; the carbonyl carbon atom is bound to a protonated nitrogen atom; the protonated nitrogen atom is bound to a parent chain; and the C3-C10 aryl, the hydrocarbon chain, and the carbonyl contain a total of at least 3 and no greater than 10 carbon atoms.

"C3-C10 arylalkyloxycarbonyl" refers to a C3-C10 aryl that is bound to any carbon atom of a branched or unbranched hydrocarbon chain by any heavy atom of the aryl, in which the hydrocarbon chain is bound to an oxygen atom by any carbon atom of the hydrocarbon chain, which is optionally the same carbon atom that is bound to the aryl; the oxygen atom is bound to a carbonyl carbon atom; the carbonyl carbon atom is bound to a parent chain; and the C3-C10 aryl, the hydrocarbon chain, and the carbonyl contain a total of at least 3 and no greater than 10 carbon atoms.

"C3-C10 arylalkylcarbamoyl" refers to a C3-C10 aryl that is bound to any carbon atom of a branched or unbranched hydrocarbon chain by any heavy atom of the aryl, in which the hydrocarbon chain is bound to a protonated nitrogen atom by any carbon atom of the hydrocarbon chain, which is optionally the same carbon atom that is bound to the aryl; the protonated nitrogen atom is bound to a carbonyl carbon atom; the carbonyl carbon atom is bound to a parent chain; and the C3-C10 aryl, the hydrocarbon chain, and the carbonyl contain a total of at least 3 and no greater than 10 carbon atoms.

"Straight or branched C1-C12 alkyl" refers to a straight or branched hydrocarbon chain that contains 1, 2, 3, 4, 5, 6, 7, 8, 9, 10, 11, or 12 carbon atoms and that is bound to a parent chain with a single bond.

"Straight or branched C1-C12 alkylidene" refers to a straight or branched hydrocarbon chain that contains 1, 2, 3, 4, 5, 6, 7, 8, 9, 10, 11, or 12 carbon atoms and that is bound to a parent chain with a double bond.

"Straight or branched C1-C12 alkyloxy" refers to a straight or branched hydrocarbon chain that contains 1, 2, 3, 4, 5, 6, 7, 8, 9, 10, 11, or 12 carbon atoms, which is bound to an oxygen atom that is bound to a parent chain.

"Straight or branched C1-C12 alkylsulfanyl" refers to a straight or branched hydrocarbon chain that contains 1, 2, 3, 4, 5, 6, 7, 8, 9, 10, 11, or 12 carbon atoms, which is bound to a sulfur atom that is bound to a parent chain.

"Straight or branched C1-C12 alkylamino" refers to a straight or branched hydrocarbon chain that contains 1, 2, 3, 4, 5, 6, 7, 8, 9, 10, 11, or 12 carbon atoms, which is bound to a protonated nitrogen atom that is bound to a parent chain.

"Straight or branched C1-C12 alkylcarbonyl" refers to a straight or branched hydrocarbon chain that contains 1, 2, 3, 4, 5, 6, 7, 8, 9, 10, or 11 carbon atoms, which t is bound to a carbonyl carbon atom that is bound to a parent chain.

"Straight or branched C1-C12 alkylcarbonyloxy" refers to a straight or branched hydrocarbon chain that contains 1, 2, 3, 4, 5, 6, 7, 8, 9, 10, or 11 carbon atoms, which is bound to a carbonyl carbon atom that is bound to an oxygen atom (other than its carbonyl oxygen atom) that is bound to a parent chain.

"Straight or branched C1-C12 alkylcarbonylsulfanyl" refers to a straight or branched hydrocarbon chain that contains 1, 2, 3, 4, 5, 6, 7, 8, 9, 10, or 11 carbon atoms, which t is bound to a carbonyl carbon atom that is bound to a sulfur atom that is bound to a parent chain.

"Straight or branched C1-C12 alkylcarbonylamino" refers to a straight or branched hydrocarbon chain that contains 1, 2, 3, 4, 5, 6, 7, 8, 9, 10, or 11 carbon atoms, which is bound to a carbonyl carbon atom that is bound to a protonated nitrogen atom that is bound to a parent chain.

"Straight or branched C1-C12 alkyloxycarbonyl" refers to a straight or branched hydrocarbon chain that contains 1, 2, 3, 4, 5, 6, 7, 8, 9, 10, or 11 carbon atoms, which is bound to an oxygen atom that is bound to a carbonyl carbon atom that is bound to a parent chain.

"Straight or branched C1-C12 alkylsulfanylcarbonyl" refers to a straight or branched hydrocarbon chain that contains 1, 2, 3, 4, 5, 6, 7, 8, 9, 10, or 11 carbon atoms, which is bound to a sulfur atom that is bound to a carbonyl carbon atom that is bound to a parent chain.

"Straight or branched C1-C12 alkylcarbamoyl" refers to a straight or branched hydrocarbon chain that contains 1, 2, 3, 4, 5, 6, 7, 8, 9, 10, or 11 carbon atoms, which is bound to a nitrogen atom that is bound to a carbonyl carbon atom that is bound to a parent chain.

"Unsubstituted" means not substituted.

"The substitution of two hydrogen atoms with a double bond" refers to the substitution of two hydrogen atoms that are bonded to two heavy atoms that are bonded to each other with a single bond with an additional bond such that, after the substitution, the two heavy atoms are bonded to each other with a double bond and each heavy atom is bonded to one less hydrogen atom.

"The substitution of a double bond with two hydrogen atoms" refers to the substitution of a double bond between two heavy atoms with two protons such that, after the substitution, each heavy atom gains a proton and the two heavy atoms are bound to each other with a single bond.

"The substitution of a hydrogen atom" refers to the substitution of a hydrogen atom with either a different atom (such as a halogen) or a group of atoms.

The substitution of two hydrogen atoms with either methylene or epoxy refers to the substitution of two hydrogen atoms that are bonded to two heavy atoms that are bonded to each other with either methylene (—$CH_2$—) or an oxygen atom (—O—) such that, after the substitution, the two heavy atoms form a 3-membered cycle with the methylene or the oxygen atom.

The substitution of two hydrogen atoms with either oxo or a substituted or unsubstituted, straight or branched C1-C12 alkylidene refers to the substitution of two hydrogen atoms that are bonded to the same heavy atom with either oxo (=O) or a substituted or unsubstituted, straight or branched C1-C12 alkylidene such that the heavy atom forms a double bond with the oxo or the alkylidene.

The co-selection of two R groups from methylene or epoxy refers to the co-selection of two R groups that are bonded to two heavy atoms that are bonded to each other from either methylene (–CH$_2$—) or an oxygen atom (—O—) such that the two heavy atoms form a 3-membered cycle with the methylene or the oxygen atom.

In some embodiments, each R group is selected such that the anion comprises at least 7 and no greater than 40 carbon atoms. In some specific embodiments, each R group is selected such that the anion comprises at least 8 and no greater than 35 carbon atoms. In some very specific embodiments, each R group is selected such that the anion comprises at least 9 and no greater than 30 carbon atoms.

In some embodiments, each R group is selected such that the anion comprises at least 6 and no greater than 50 hydrogen atoms. In some specific embodiments, each R group is selected such that the anion comprises at least 7 and no greater than 45 hydrogen atoms. In some very specific embodiments, each R group is selected such that the anion comprises at least 8 and no greater than 40 hydrogen atoms.

In some embodiments, each R group is selected such that the anion comprises at least 1 and no greater than 10 oxygen atoms. In some specific embodiments, each R group is selected such that the anion comprises at least 1 and no greater than 9 oxygen atoms. In some very specific embodiments, each R group is selected such that the anion comprises at least 1 and no greater than 8 oxygen atoms.

In some embodiments, each R group is selected such that the anion comprises no greater than 5 total combined sulfur, nitrogen, and halogen atoms. In some specific embodiments, each R group is selected such that the anion comprises no greater than 3 total combined sulfur, nitrogen, and halogen atoms. In some very specific embodiments, each R group is selected such that the anion comprises either 1 sulfur atom, 1 nitrogen atom, or 1 halogen atom.

In some embodiments, each skeletal atom is a carbon atom except that one or two asterisks (*) depict an independent, optional substitution of a skeletal atom with either an oxygen atom; each R group that occurs, other than the R group that is oxide, is independently selected from H; a halogen; hydroxy; oxo; formyl; a substituted or unsubstituted C3-C10 cycloalkyl, aryl, or arylalkyl; and a substituted or unsubstituted, straight or branched C1-C12 alkyl, alkyloxy, alkylcarbonyl, alkyloxycarbonyl, or alkylcarbonyloxy, wherein substitutions are limited to (i) the substitution of two hydrogen atoms with a double bond, oxo, methylidene, methylene, epoxy, or methylenedioxy (ii) the substitution of a double bond with two hydrogen atoms, (iii) the substitution of a hydrogen atom with a halogen; hydroxy; or a substituted or unsubstituted methyl, ethyl, propyl, butyl, pentyl, hexyl, heptyl, octanyl, nonanyl, decanyl, undecanyl, dodecanyl, cyclohexyl, phenyl, benzyl, 4H-chromen-2-yl, or 4H-chromen-3-yl, and (vi) the substitution of a methylene bridge with an oxygen atom, except that two R groups may be optionally co-selected from methylene, epoxy, and methylenedioxy.

In some specific embodiments, each R group that occurs, other than the R group that is oxide, is independently selected from H; methyl; ethyl; propyl; butyl; pentyl; hexyl; heptyl; ethenyl; ethynyl; prop-1-enyl; propen-2-yl; isoprenyl; geranyl; a halogen; hydroxy; methoxy; ethoxy; 2-propoxy; oxo; formyl; acetyl; propionyl; 2-oxo-propyl; butyryl; 3-oxo-butyl; phenyl; benzyl; phenylcarbonyl; 2-phenylethyl; 2-phenylethenyl; 3-phenylprop-2-enonyl; and a methyl, ethyl, propyl, butyl, pentyl, hexyl, heptyl, acetyl, propionyl, 2-oxo-propyl, butyryl, 3-oxo-butyl, phenyl, benzyl, phenylcarbonyl, 2-phenylethyl, 2-phenylethenyl, or 3-phenylprop-2-enonyl that is substituted with 1, 2, or 3 groups selected from methyl, ethyl, propyl, a halogen, hydroxy, methoxy, ethoxy, and 2-propoxy.

In some very specific embodiments, each R group that occurs, other than the R group that is oxide, is independently selected from H; methyl; ethyl; ethenyl; ethynyl; isoprenyl; geranyl; a halogen; hydroxy; methoxy; oxo; formyl; acetyl; propionyl; 2-oxo-propyl; butyryl; 3-oxo-butyl; phenyl; benzyl; phenylcarbonyl; 2-phenylethyl; 3-phenylprop-2-enonyl; and a methyl, ethyl, ethenyl, acetyl, propionyl, 2-oxo-propyl, butyryl, 3-oxo-butyl, phenyl, benzyl, phenylcarbonyl, 2-phenylethenyl, or 3-phenylprop-2-enonyl that is substituted with 1, 2, or 3 groups selected from methyl, a halogen, hydroxy, and methoxy.

In some embodiments, each R group that occurs, other than the R group that is oxide, is independently selected from H; methyl; ethyl; ethyenyl; ethynyl; prop-2-yl; propen-2-yl; isoprenyl;
geranyl; oxo; formyl; acetyl; and methoxy.

In some embodiments, the anion has the general formula XXXVII. In some specific embodiments, the anion has the general formula XXXVII; and the R25 group is the oxide group of the anion.

In some embodiments, the anion is (8R,9S,13S,14S,17S)-17-hydroxy-13-methyl-6,7,8,9,11,12,14,15,16,17-decahydro-cyclopenta[a]phenanthrene-3-oxide.

In some embodiments, the anion is (8R,9S,13S,14S,17R)-17-hydroxy-17-ethynyl-13-methyl-7,8,9,11,12,14,15,16-octahydro-6H-cyclopenta[a]phenanthrene-3-oxide.

In some embodiments, anion has the general formula III. In some specific embodiments, the anion has the general formula III; and the R7 group is the oxide group of the anion.

In some embodiments, the anion is 2-oxo-3-(1-phenyl-prop-1-yl)-2H-chromene-4-oxide.

In some embodiments, the anion has the general formula I.

In some embodiments, the anion is 2,6-di(prop-2-yl)-benzene-1-oxide.

In some embodiments, the anion has the general formula V. In some specific embodiments, the anion has the general formula V; R1, R7, and R11 are independently selected from H and methyl; and the dotted lines labeled with DD and LL are either both single bonds or both double bonds.

In some embodiments, the anion is selected from (2R)-2,5,7-trimethyl-2-[(4R,8R)-4,8,12-trimethyl-tridecyl]-3,4-dihydrochromen-6-oxide; (2R)-2,7-dimethyl-2-[(4R,8R)-4,8,12-trimethyl-tridecyl]-3,4-dihydrochromen-6-oxide; (2R)-2,5,7,8-tetramethyl-2-[(4R,8R)-4,8,12-trimethyl-tridecyl]-3,4-dihydrochromen-6-oxide; (2R)-2,5,8-trimethyl-2-[(4R,8R)-4,8,12-trimethyl-tridecyl]-3,4-dihydrochromen-6-oxide; (2R)-2,7,8-trimethyl-2-[(4R,8R)-4,8,12-trimethyl-tridecyl]-3,4-dihydrochromen-6-oxide; (2R)-2,8-dimethyl-2-[(4R,8R)-4,8,12-trimethyl-tridecyl]-3,4-dihydrochromen-6-oxide; (2R)-2,5,7,8-tetramethyl-2-[(3E,7E)-4,8,12-trimethyl-trideca-3,7,11-triene-1-yl]-3,4-dihydrochromen-6-oxide; and (2R)-2,5,8-trimethyl-2-[(3E,7E)-4,8,12-trimethyl-trideca-3,7,11-triene-1-yl]-3,4-dihydrochromen-6-oxide.

In some embodiments, the anion has the general formula VII. In some specific embodiments, the anion has the general formula VII; each skeletal atom is a carbon atom; and each R group other than the R group that is oxide is independently selected from H, F, hydroxy, methoxy, methyl, ethyl, and ethylidene.

In some embodiments, the anion is selected from 3-hydroxy-5-[(E)-2-(4-hydroxyphen-1-yl)-ethen-1-yl]-benzene-1-oxide and 4-[(E)-2-(3,5-hydroxy-phen-1-yl)-ethen-1-yl]-benzene-1-oxide.

In some embodiments, the anion has the general formula XIII. In some specific embodiments, the anion has the general formula XIII; exactly one skeletal atom that is marked with an asterisk (*) is substituted with oxygen; and each R group other than the R group that is oxide is independently selected from H, hydroxy, methoxy, methyl, oxo, isoprenyl, and geranyl.

In some embodiments, the anion is selected from benzestrol anion: 4-[4-ethyl-5-(4-hydroxyphen-1-yl)-hexan-3-yl]-benzene-1-oxide or 4-[3-ethyl-4-(4-hydroxyphen-1-yl)-hexan-2-yl]-benzene-1-oxide; bromosaligenin anion: 4-bromo-2-(hydroxymethyl)-benzene-1-oxide; chlorindanol anion: 7-chloro-2,3-dihydro-1H-inden-4-oxide; cotoin anion: 3-hydroxy-5-methoxy-2-(phenylcarbonyl)-benzene-1-oxide; irisolone anion: 4-(8-oxo-9-methoxy-[1,3]diolxolo[4,5-g]-4H-chromen-7-yl)-benzene-1-oxide; procerin anion: 7-oxo-4-(3-methyl-but-2-en-1-yl)-5-(prop-1-en-2-yl)-cyclohepta-1,3,5-trien-1-oxide; psoralidin anion: 3-hydroxy-6-oxo-2-(3-methyl-but-2-en-1yl)-benzofurano[3,2-c]chromen-9(6H)-oxide or 9-hydroxy-6-oxo-2-(3-methyl-but-2-en-lyl)-benzofurano[3,2-c]chromen-3(6H)-oxide; sumatrol anion: 6-oxo-1,2,6,6a,12,12a-hexahydro-2-isopropenyl-8,9-dimethoxychromeno[3,4-b]furo[2,3-h]chromene-5-oxide; zeta2-tocopherol anion: (2R)-2,5,7-trimethyl-2-[(4R,8R)-4,8,12-trimethyl-tridecyl]-3,4-dihydrochromen-6-oxide; eta-tocopherol anion: (2R)-2,7-dimethyl-2-[(4R,8R)-4,8,12-trimethyl-tridecyl]-3,4-dihydrochromen-6-oxide; benzarone anion: 4-[(2-ethyl-1-benzofuran-3-yl)-carbonyl]-benzene-1-oxide; coumafuryl anion: 2-oxo-3-[3-oxo-1-(furan-2-yl)-but-1-yl]-2H-chromene-4-oxide; fuscin anion: 4,8,8-trimethyl-5,6-dioxo-9,10-dihydro-4H-pyrano[3,2-f]isochromene-2-oxide; gentisyl alcohol anion: 3-(hydroxymethyl)-4-hydroxy-benzene-1-oxide or 2-(hydroxymethyl)-4-hydroxy-benzene-1-oxide; morphenol anion: phenanthro[4,5-bcd]furan-3-oxide; osajin anion: 4-[4-oxo-5-hydroxy-8,8-dimethyl-6-(3-methyl-but-2-en-1-yl)-pyrano[2,3-h]-4H-chromen-3-yl]-benzene-1-oxide or 4-oxo-3-(4-hydroxyphen-1-yl)-8,8-dimethyl-6-(3-methyl-but-2-en-1-yl)-pyrano[2,3-h]-4H-chromene-5-oxide; actiphenol anion: 4,6-dimethyl-2-[1-oxo-2-(2,6-dioxo-piperidin-4-yl)-eth-1-yl]-benzene-1-oxide; anthrarobin anion: 2,10-dihydroxy-anthracene-1-oxide, 1,2-dihydroxy-anthracene-10-oxide, or 1,10-dihydroxy-anthracene-2-oxide; bifluranol anion: 2-fluoro-4-[2-(3-fluoro-4-hydroxyphen-1-yl)-pentan-3-yl]-benzene-1-oxide or 2-fluoro-4-[3-(3-fluoro-4-hydroxyphen-1-yl)-pentan-2-yl]-benzene-1-oxide; bromosalicylchloranilide anion: (3-bromo-6-oxo-cyclohexa-2,4-dien-1-ylidene)-N-(4-chlorophen-1-yl)-aminomethane-oxide or 5-bromo-N-(4-chlorophen-1-yl)-benzamide-2-oxide; cyclovalone anion: 2-methoxy-4-({2-oxo-3-[(3-methyoxy-4-hydroxyphen-1-yl)-methylidene]-cyclohex-1-ylidene}-methyl)-benzene-1-oxide; protiofate anion: 4-hydroxy-2,5-bis(propoxycarbonyl)-thiophene-3-oxide; acacetin anion: 7-hydroxy-4-oxo-2-(4-methoxy-phen-1-yl)-4H-chromene-5-oxide or 5-hydroxy-4-oxo-2-(4-methoxy-phen-1-yl)-4H-chromene-7-oxide; albofungin anion: 14,17-dioxo-13-amino-3,4,8a,13-tetrahydro-1,16-dihydroxy-4-methoxy-12-methyl-1H-xantheno(4',3',2':4,5)(1,3)benzodioxino(7,6-g)isoquinoline-15(2H,9H)-oxide or 14,17-dioxo-13-amino-3,4,8a,13-tetrahydro-1,15-dihydroxy-4-methoxy-12-methyl-1H-xantheno(4',3',2':4,5)(1,3)benzodioxino(7,6-g)isoquinoline-16(2H,9H)-oxide; alizarin anion: 2-hydroxy-9,10-dioxo-anthracene-1-oxide or 1-hydroxy-9,10-dioxo-anthracene-2-oxide; alizarin 1-methyl ether anion: 1-methoxy-9,10-dioxo-anthracene-2-oxide; alizarin 2-methyl ether anion: 2-methoxy-9,10-dioxo-anthracene-1-oxide; alkannin anion: 4-hydroxy-5,8-dioxo-6-[(1S)-1-hydroxy-4-methylpent-3-en-1-yl]-naphthalene-1-oxide or 4-hydroxy-5,8-dioxo-7-[(1S)-1-hydroxy-4-methylpent-3-en-1-yl]-naphthalene-1-oxide; aloe emodin anion: 8-hydroxy-6-(hydroxymethyl)-9,10-dioxo-anthracene-1-oxide or 8-hydroxy-3-(hydroxymethyl)-9,10-dioxo-anthracene-1-oxide; ampelopsin anion: (2R,3R)-4-oxo-3,5-dihydroxy-2-(3,4,5-trihydroxy-phen-1-yl)-2,3-dihydro-4H-chromene-7-oxide, 2,6-dihydroxy-4-[(2R,3R)-4-oxo-3,5,7-trihydroxy-2,3-dihydro-4H-chromen-2-yl]-benzene-1-oxide, 2,3-dihydroxy-5-[(2R,3R)-4-oxo-3,5,7-trihydroxy-2,3-dihydro-4H-chromen-2-yl]-benzene-1-oxide, or (2R,3R)-4-oxo-3,7-dihydroxy-2-(3,4,5-trihydroxy-phen-1-yl)-2,3-dihydro-4H-chromene-5-oxide; para-anol anion: 4-(prop-1-en-1-yl)-benzene-1-oxide; anthragallol anion: 2,3-dihydroxy-9,10-dioxo-anthracene-1-oxide, 3,4-dihydroxy-9,10-dioxo-anthracene-2-oxide, or 1,3-dihydroxy-9,10-dioxo-anthracene-2-oxide; anthralin anion: 8-hydroxy-9-oxo-9,10-dihydroanthracen-1-oxide; anthranol anion: anthracen-9-oxide; anthrarufin anion: 5-hydroxy-9,10-dioxo-anthracene-1-oxide; apigenin anion: 4-oxo-5-hydroxy-2-(4-hydroxyphen-1-yl)-4H-chromene-7-oxide, 4-(4-oxo-5,7-dihydroxy-4H-chromen-2-yl)-benzene-1-oxide, or 4-oxo-7-hydroxy-2-(4-hydroxyphen-1-yl)-4H-chromene-5-oxide; apocynin anion: 2-methoxy-4-(1-oxo-eth-1-yl)-benzene-1-oxide; aspidinol anion: 3-hydroxy-2-(1-oxo-but-1-yl)-6-methyl-5-methoxy-benzene-1-oxide or 3-hydroxy-2-(1-oxo-but-1-yl)-4-methyl-5-methoxy-benzene-1-oxide; atovaquone anion: 2-[4-(4-chlorophen-1-yl)-cyclohex-1-yl]-3,4-dioxo-naphthalene-1-oxide; atranorin anion: 6-formyl-5-hydroxy-2-{[(3-hydroxy-4-methoxycarbonyl-2,5-dimethylphen-1-yl)-oxy]-carbonyl}-3-methylbenzene-1-oxide, 6-methoxycarbonyl-3-{[(3-formyl-2,4-dihydroxy-6-methylphen-1-yl)-carbonyl]-oxy}-2,5-dimethylbenzene-1-oxide, or 2-formyl-3-hydroxy-4-{[(3-hydroxy-4-methoxycarbonyl-2,5-dimethylphen-1-yl)-oxy]-carbonyl}-5-methylbenzene-1-oxide; baicalein anion: 5,7-hydroxy-4-oxo-2-phenyl-4H-chromen-6-oxide, 6,7-hydroxy-4-oxo-2-phenyl-4H-chromene-5-oxide, or 5,6-hydroxy-4-oxo-2-phenyl-4H-chromene-7-oxide; baptigenin anion: 2,3-dihydroxy-5-(4-oxo-7-hydroxy-4H-chromen-3-yl)-benzene-1-oxide, 2,6-dihydroxy-4-(4-oxo-7-hydroxy-4H-chromen-3-yl)-benzene-1-oxide, or 4-oxo-3-(3,4,5-trihydroxy-phen-1-yl)-4H-chromene-7-oxide; benzbromarone anion: 4-[(2-ethyl-1-benzofuran-3-yl)-carbonyl]-2,6-dibromo-benzene-1-oxide; benziodarone anion: 4-[(2-ethyl-1-benzofuran-3-yl)-carbonyl]-2,6-diiodo-benzene-1-oxide; benzophenone-6 anion: (2-hydroxy-4-methoxyphen-1-yl)-(6-oxo-2-methoxycyclohexa-1,3-dien-5-ylidene)-methane-oxide or 5-methoxy-2-[(2-hydroxy-4-methoxy-phen-1-yl)-carbonyl]-benzene-1-oxide; benzoresorcinol anion: 3-hydroxy-6-(phenylcarbonyl)-benzene-1-oxide or 3-hydroxy-4-(phenylcarbonyl)-benzene-1-oxide; ortho-benzylphenol anion: 2-benzyl-benzene-1-oxide; para-benzylphenol anion: 4-benzyl-benzene-1-oxide; biochanin A anion: 7-hydroxy-4-oxo-3-(4-methoxy-phen-1-yl)-4H-chromene-5-oxide or 5-hydroxy-4-oxo-3-(4-methoxy-phen-1-yl)-4H-chromene-7-oxide; bisphenol A anion: 4-[2-(4-hydroxy-phen-1-yl)-propan-2-yl]-benzene-1-oxide; bisphenol B anion: 4-[2-(4-hydroxy-phen-1-yl)-butan-2-yl]-benzene-1-oxide; brazilin anion: (6aS, 11bR)-3,6a, 10-trihydroxy-7,11b-dihydro-6H-indeno[2,1-c]chromene-9-oxide; brodifacoum anion: 2-oxo- 3-{3-[4-(4-bromo-phen-1-yl)-phen-1-yl]-1,2,3,4-tetrahydro-naphthalen-1-yl}-2H-chromene-4-oxide; bromadiolone anion: 2-oxo-3-{3-hydroxy-3-[4-(4-bromo-phen-1-yl)-phen-1-yl]-1-phenyl-prop-1-yl}-2H-chromene-4-oxide; buparvaquone anion: 2-[(4-tert-butyl-cyclohex-1-yl)-methyl]-3,4-dioxo-naphthalene-1-oxide; butylated hydroxyanisole anion: 3-tert-butyl-4-methoxy-benzene-1-oxide or 2-tert-butyl-4-methoxy-benzene-1-oxide; butylated hydroxytoluene anion: 2,6-di-tert-butyl-4-methyl-benzene-1-oxide; butylparaben anion: 4-(butoxy-carbonyl)-benzene-1-oxide; cabenegrin A-I anion: 4-[(2E)-4-hydroxy-3-methyl-but-2-en-1-yl]-6a,12a-dihydro-(1,3)dioxolo(5,6)[1]benzofuro[3,2-c]chromen-3(6H)-oxide; cabenegrin A-II anion: 2-[4-hydroxy-3-methyl-but-1-yl]-6a,12a-dihydro-(1,3)dioxolo(5,6)[1]benzofuro[3,2-c]chromen-3(6H)-oxide; cannabidiol anion: 3-hydroxy-2-[(1R,6R)-6-(prop-1-en-2-yl)-3-methyl-cyclohex-2-en-1-yl]-5-pentyl-benzene-1-oxide; 4'-fluorocannabidiol anion: 3-hydroxy-2-[(1R,6R)-6-(prop-1-en-2-yl)-3-methyl-cyclohex-2-en-1-yl]-6-fluoro-5-pentyl-benzene-1-oxide or 3-hydroxy-2-[(1R,6R)-6-(prop-1-en-2-yl)-3-methyl-cyclohex-2-en-1-yl]-4-fluoro-5-pentyl-benzene-1-oxide; cannabidivarin anion: 3-hydroxy-2-[(1R,6R)-6-(prop-1-en-2-yl)-3-methyl-cy cl ohex-2-en-1-yl]-5-propyl-benzene-1-oxide; cannabidiphorol anion: 3-hydroxy-2-[(1R,6R)-6-(prop-1-en-2-yl)-3-methyl-cyclohex-2-en-1-yl]-5-heptyl-benzene-1-oxide; dimethylheptyl cannabidiol anion: 3-hydroxy-2-[(1R,6R)-6-(prop-1-en-2-yl)-3-methyl-cyclohex-2-en-1-yl]-5-(2-methyl-octan-2-yl)-benzene-1-oxide; cannabinol anion: 6,6,9-trimethyl-3-pentyl-benzo[c]chromene-1-oxide; carvacrol anion: 2-methyl-5-(propan-2-yl)-benzene-1-oxide; catechin anion: (2R,3S)-3,7-dihydroxy-2-(3,4-dihydroxy-phen-1-yl)-3,4-dihydro-2H-chromene-5-oxide, 2-hydroxy-4-[(2R,3S)-3,5,7-trihydroxy-3,4-dihydro-2H-chromen-2-yl]-benzene-1-oxide, 2-hydroxy-5-[(2R,3S)-3,5,7-trihydroxy-3,4-dihydro-2H-chromen-2-yl]-benzene-1-oxide, or (2R,3S)-3,5-dihydroxy-2-(3,4-dihydroxy-phen-1-yl)-3,4-dihydro-2H-chromene-7-oxide; epicatechin anion: (2R,3R)-3,7-dihydroxy-2-(3,4-dihydroxy-phen-1-yl)-3,4-dihydro-2H-chromene-5-oxide, 2-hydroxy-4-[(2R,3R)-3,5,7-trihydroxy-3,4-dihydro-2H-chromen-2-yl]-benzene-1-oxide, 2-hydroxy-5-[(2R,3R)-3,5,7-trihydroxy-3,4-dihydro-2H-chromen-2-yl]-benzene-1-oxide, or (2R,3R)-3,5-dihydroxy-2-(3,4-dihydroxy-phen-1-yl)-3,4-dihydro-2H-chromene-7-oxide; gallocatechin anion: (2R,3S)-3,7-dihydroxy-2-(3,4,5-trihydroxy-phen-1-yl)-3,4-dihydro-2H-chromene-5-oxide, 2,6-dihydroxy-4-[(2R,3S)-3,5,7-trihydroxy-3,4-dihydro-2H-chromen-2-yl]-benzene-1-oxide, 2,3-dihydroxy-5-[(2R,3S)-3,5,7-trihydroxy-3,4-dihydro-2H-chromen-2-yl]-benzene-1-oxide, or (2R,3S)-3,5-dihydroxy-2-(3,4,5-trihydroxy-phen-1-yl)-3,4-dihydro-2H-chromene-7-oxide; epigallocatechin anion: (2R,3R)-3,7-dihydroxy-2-(3,4,5-trihydroxy-phen-1-yl)-3,4-dihydro-2H-chromene-5-oxide, 2,6-dihydroxy-4-[(2R,3R)-3,5,7-trihydroxy-3,4-dihydro-2H-chromen-2-yl]-benzene-1-oxide, 2,3-dihydroxy-5-[(2R,3R)-3,5,7-trihydroxy-3,4-dihydro-2H-chromen-2-yl]-benzene-1-oxide, or (2R,3R)-3,5-dihydroxy-2-(3,4,5-trihydroxy-phen-1-yl)-3,4-dihydro-2H-chromene-7-oxide; ourateacatechin anion: (2R,3R)-3,7-dihydroxy-2-(3,5-dihydroxy-4-methoxy-phen-1-yl)-3,4-dihydro-2H-chromene-5-oxide, 2-methoxy-3-hydroxy-5-[(2R,3R)-3,5,7-trihydroxy-3,4-dihydro-2H-chromen-2-yl]-benzene-1-oxide, or (2R,3R)-3,5-dihydroxy-2-(3,5-dihydroxy-4-methoxy-phen-1-yl)-3,4-dihydro-2H-chromene-7-oxide; chavicol anion: 4-(prop-2-en-1-yl)-benzene-1-oxide; chrysarobin anion: 9-oxo-8-hydroxy-6-methyl-10H-anthracen-1-oxide or 9-oxo-8-hydroxy-3-methyl-10H-anthracen-1-oxide; chrysin anion: 7-hydroxy-4-oxo-2-phenyl-4H-chromene-5-oxide or 5-hydroxy-4-oxo-2-phenyl-4H-chromene-7-oxide; methylchrysin anion: 7-hydroxy-4-oxo-2-phenyl-3-methyl-4H-chromene-5-oxide or 5-hydroxy-4-oxo-2-phenyl-3-methyl-4H-chromene-7-oxide; clofoctol anion: 2-[(2,4-di chlorophen-1-yl)-methyl]-4-(2,4,4-trimethylpent-2-yl)-benzene-1-oxide; clorophene anion: 2-benzyl-4-chloro-benzene-1-oxide; collinomycin anion: 3-(methoxycarbonyl)-6-[2-(4,9-dihydro-8-hydroxy-5,7-dimethoxy-4,9-dioxo-benzo[f][1]benzofuran-2-yl)-eth-1-yl]-8-hydroxy-1-oxo-1H-2-benzopyran-8-oxide, 2-{[3-(methoxycarbonyl)-7,8-dihydroxy-1-oxo-1H-2-benzopyran-6-yl]-eth-1-yl}-4,9-dihydro-5,7-dimethoxy-4,9-dioxo-benzo[f][1]benzofuran-8-oxide, or 3-(methoxycarbonyl)-6-[2-(4,9-dihydro-8-hydroxy-5,7-dimethoxy-4,9-dioxo-benzo[f][1]benzofuran-2-yl)-eth-1-yl]-8-hydroxy-1-oxo-1H-2-benzopyran-7-oxide; combretastatin anion: 2-methoxy-5-[2-hydroxy-2-(3,4,5-trimethoxy-phen-1-yl)-eth-1-yl]-benzene-1-oxide; combretastatin A-1 anion: 2-hydroxy-6-methoxy-3-[(E)-2-(3,4,5-trimethoxy-phen-1-yl)-ethen-1-yl]-benzene-1-oxide or 2-hydroxy-3-methoxy-6-[(E)-2-(3,4,5-trimethoxy-phen-1-yl)-ethen-1-yl]-benzene-1-oxide; combretastatin A-4 anion: 2-methoxy-5-[(Z)-2-(3,4,5-trimethoxy-phen-1-yl)-ethen-1-yl]-benzene-1-oxide; combretastatin B-1 anion: 2-hydroxy-6-methoxy-3-[2-(3,4,5-trimethoxy-phen-1-yl)-eth-1-yl]-benzene-1-oxide or 2-hydroxy-3-methoxy-6-[2-(3,4,5-trimethoxy-phen-1-yl)-eth-1-yl]-benzene-1-oxide; coniferyl alcohol anion: 4-[(E)-3-hydroxy-prop-1-en-1-yl]-2-methoxy-benzene-1-oxide; coumestrol anion: 3-hydroxy-6-oxo-benzofurano[3,2-c]chromen-9(6H)-oxide or 9-hydroxy-6-oxo-benzofurano[3,2-c]chromen-3(6H)-oxide; ortho-cresol anion: 2-methyl-benzene-1-oxide; meta-cresol anion: 3-methyl-benzene-1-oxide; para-cresol anion: 4-methyl-benzene-1-oxide; curcumin anion: 2-methoxy-4-[7-(4-hydroxy-3-methoxy-phen-1-yl)-3,5-dioxo-hepta-1,6-diene-1-yl]-benzene-1-oxide; curvularin anion: 3,11-dioxo-15-hydroxy-5-methyl-4-oxa-bicyclo[10.4.0]hexadeca-1(12),13,15-triene-13-oxide or 3,11-dioxo-13-hydroxy-5-methyl-4-oxa-bicyclo[10.4.0]hexadeca-1(12),13,15-triene-15-oxide; daidzein anion: 4-(4-oxo-7-hydroxy-4H-chromen-3-yl)-benzene-1-oxide or 4-oxo-3-(4-hydroxyphenyl)-4H-chromene-7-oxide; danthron anion: 8-hydroxy-9,10-dioxo-anthracene-1-oxide; daphnetin anion: 7-hydroxy-2-oxo-2H-chromen-8-oxide or 8-hydroxy-2-oxo-2H-chromene-7-oxide; datiscetin anion: 3,7-dihydroxy-4-oxo-2-(2-hydroxy-phen-1-yl)-4H-chromene-5-oxide, 3,5-dihydroxy-4-oxo-2-(2-hydroxy-phen-1-yl)-4H-chromene-7-oxide, 2-(3,5,7-trihydroxy-4-oxo-4H-chrom en-2-yl)-benzene-1-oxide, or 5,7-dihydroxy-4-oxo-2-(2-hydroxy-phen-1-yl)-4H-chromen-3-oxide; 4,6-di-tert-butyl-meta-cresolanion-2,4-di-tert-butyl-5-methyl-benzene-1-oxide; deferiprone anion: 4-oxo-1,2-dimethyl-pyridin-3(1H)-oxide; dehydroequol anion: 4-(7-hydroxy-2H-chromen-3-yl)-benzene-1-oxide or 3-(4-hydroxy-phen-1-yl)-2H-chromene-7-oxide; dexanabinol anion: (6aS,10aS)-6,6-dimethyl-9-(hydroxymethyl)-3-(2-methyl-octan-2-yl)-6a,7,10,10 a-tetrahy dro-6H-benzo[c]chromene-1-oxide; 2',7'-dichlorofluorescein anion: 2',7'-dichloro-6'-hydroxy-3-oxo-spiro(2-benzofuran-1,9'-xanthene)-3'-oxide; 4',5'-dichlorofluorescein anion: 4',5'-dichloro-6'-hydroxy-3-oxo-spiro(2-benzofuran-1,9'-xanthene)-3'-oxide; dichlorophen anion: 4-chloro-2-[(5-chloro-2-hydroxyphen-1-yl)-methyl]-benzene-1-oxide; dicoumarol anion: 2-oxo-3-[(4-hydroxy-2-oxo-2H-chromen-3-yl)-methyl]-2H-chromene-4-oxide; dienestrol anion: 4-[4-(4-hydroxy-phen-1-yl)-hexa-2,4-dien-3-yl]-benzene-1-oxide; diethylstilbestrol anion: 4-[4-(4-hydroxy-phen-1-yl)-hex-3-en-3-yl]-benzene-1-oxide; mestilbol anion: 4-[4-(4-methoxy-phen-1-yl)-hex-3-en- 3-yl]-phenol; diethylstilbestrol monobenzyl ether anion: 4-[4-(4-phenylmethoxy-phen-1-yl)-hex-3-en-3-yl]-benzene-1-oxide; stilbestrol anion: 4-[2-(4-hydroxy-phen-1-yl)-ethen-1-yl]-benzene-1-oxide; dimethylstilbestrol anion: 4-[3-(4-hydroxy-phen-1-yl)-but-2-en-2-yl]-benzene-1-oxide; difenacoum anion: 2-oxo-3-[3-(4-phenyl-phen-1-yl)-1,2,3,4-tetrahy dro-naphthal en-1-yl]-2H-chromene-4-oxide; 17alpha-dihydroequilin anion: (9S,13S,14S,17R)-17-hydroxy-13-methyl-6,9,11,12,14,15,16,17-octahydro-cyclopenta[a]phenanthrene-3-oxide; 17beta-dihydroequilin anion: (9S,13S,14S,17S)-17-hydroxy-13-methyl-6,9,11,12,14,15,16,17-octahy dro-cyclopenta[a]phenanthrene-3-oxide; 4',5-diiodofluorescein anion: 4',5'-diiodo-6'-hydroxy-3-oxo-spiro(2-benzofuran-1,9'-xanthene)-3'-oxide; dioxybenzone anion: 3-methoxy-6-[(2-hydroxyphen-1-yl)-carbonyl]-benzene-1-oxide or 2-[(2-hydroxy-4-methoxy-phen-1-yl)-carbonyl]-benzene-1-oxide; 2,5-di-tert-pentyl-hydroquinone anion: 2,5-bis(2-methylbutan-2-yl)-4-hydroxy-benzene-1-oxide; epigallocatechin gallate anion: 2,6-dihydroxy-4-({[(2R,3R)-5,7-dihydroxy-2-(3,4,5-trihydroxy-phen-1-yl)-3,4-dihydro-2H-chromen-3-yl]-oxy}-carbonyl)-benzene-1-oxide, (2R,3R)-7-hydroxy-2-(3,4,5-trihydroxy-phen-1-yl)-3-{[(3,4,5-trihydroxy-phen-1-yl)-carbonyl]-oxy}-3,4-dihydro-2H-chromene-5-oxide, (2R,3R)-5-hydroxy-2-(3,4,5-trihydroxy-phen-1-yl)-3-{[(3,4,5-trihydroxy-phen-1-yl)-carbonyl]-oxy}-3,4-dihydro-2H-chromene-7-oxide, 2,3-dihydroxy-5-[(2R,3R)-5,7-dihydroxy-3-{[(3,4,5-trihydroxy-phen-1-yl)-carbonyl]-oxy}-3,4-dihydro-2H-chromen-2-yl]-benzene-1-oxide, 2,6-dihydroxy-4-[(2R,3R)-5,7-dihydroxy-3-{[(3,4,5-trihydroxy-phen-1-yl)-carbonyl]-oxy}-3,4-dihydro-2H-chromen-2-yl]-benzene-1-oxide, or 2,3-dihydroxy-5-({[(2R,3R)-5,7-dihydroxy-2-(3,4,5-trihydroxy-phen-1-yl)-3,4-dihydro-2H-chromen-3-yl]-oxy}-carbonyl)-benzene-1-oxide; embelin anion: 5-hydroxy-4-undecyl-1,4-benzoquinone-3-oxide or 5-hydroxy-3-undecyl-1,4-benzoquinone-2-oxide; emodin anion: 3,8-dihydroxy-6-methyl-9,10-dioxo-anthracene-1-oxide, 6,8-dihydroxy-3-methyl-9,10-dioxo-anthracene-1-oxide, or 4,5-dihydroxy-7-methyl-9,10-dioxo-anthracene-2-oxide; parietin anion: 8-hydroxy-6-methoxy-3-methyl-9,10-dioxo-anthracene-1-oxide or 8-hydroxy-3-methoxy-6-methyl-9,10-dioxo-anthracene-1-oxide; enterolactone anion: 3-({2-oxo-5-[(3-hydroxyphen-1-yl)-methyl]-3-oxacyclopent-1-yl}-methyl)-benzene-1-oxide or 3-({4-oxo-5-[(3-hydroxyphen-1-yl)-methyl]-3-oxacyclopent-1-yl}-methyl)-benzene-1-oxide; 16-epiestriol anion: (8R,9S,13S,14S,16S,17R)-16,17-dihydroxy-13-methyl-6,7,8,9,11,12,14,15,16,17-decahydro-cyclopenta[a]phenanthrene-3-oxide; equilenin anion: (13S,14S)-17-oxo-13-methyl-12,14,15,16-tetrahydro-11H-cyclopenta[a]phenanthrene-3-oxide; equilin anion: (9S,13S,14S)-17-oxo-13-methyl-9,11,12,14,15,16-hexahydro-6H-cyclopenta[a]phenanthrene-3-oxide; equol anion: 4-[(3S)-7-hydroxy-3,4-dihydro-2H-chromen-3-yl]-benzene-1-oxide or (3S)-3-(4-hydroxyphen-1-yl)-3,4-dihydro-2H-chromene-7-oxide; ergoflavin anion: 9,11-dioxo-4,9a-trihydroxy-3-methyl-1,4a-oxycarbonyl-7-[9,11-dioxo-4,8,9a-trihydroxy-3-methyl-1,4a-oxycarbonyl-1,3,4,9a-tetrahydro-[4a1-1]-xanthen-7(2H)-yl]-1,3,4,9a-tetrahydro-[4a1-1]-xanthene-8(2H)-oxide; eriodictyol anion: (2S)-7-hydroxy-4-oxo-2-(3,4-dihydroxy-phen-1-yl)-2,3-dihydro-4H-chromene-5-oxide, 2-hydroxy-4-[(2S)-5,7-dihydroxy-4-oxo-2,3-dihydro-4H-chromene-2-yl]-benzene-1-oxide, 2-hydroxy-5-[(2S)-5,7-dihydroxy-4-oxo-2,3-dihydro-4H-chromene-2-yl]-benzene-1-oxide, or (2S)-5-hydroxy-4-oxo-2-(3,4-dihydroxy-phen-1-yl)-2,3-dihydro-4H-chromene-7-oxide; esculetin anion: 7-hydroxy-2-oxo-2H-chromen-6-oxide or 6-hydroxy-2-oxo-2H-chromene-7-oxide; estradiol anion: (8R,9S,13S,14S,17S)-17-hydroxy-13-methyl-6,7,8,9,11,12,14,15,16,17-decahydro-cyclopenta[a]phenanthrene-3-oxide; estradiol valerate anion: (8R,9S,13S,14S,17S)-13-methyl-17-[(1-oxo-pent-1-yl)-oxy]-6,7,8,9,11,12,14,15,16,17-decahydro-cyclopenta[a]phenanthrene-3-oxide; estradiol enanthate anion: (8R,9S,13S,14S,17S)-13-methyl-17-[(1-oxo-hept-1-yl)-oxy]-6,7,8,9,11,12,14,15,16,17-decahydro-cyclopenta[a]phenanthrene-3-oxide; estradiol 17(3-cyclopentanepropanoate anion: (8R,9S,13S,14S,17S)-13-methyl-17-[(1-oxo-3-cyclopentylprop-1-yl)-oxy]-6,7,8,9,11,12,14,15,16,17-decahydro-cyclopenta[a]phenanthrene-3-oxide; estradiol undecylate anion: (8R,9S,13S,14S,17S)-13-methyl-17-[(1-oxo-undecan-1-yl)-oxy]-6,7,8,9,11,12,14,15,16,17-decahydro-cyclopenta[a]phenanthrene-3-oxide; alpha-estradiol anion: (8R,9S,13S,14S,17R)-17-hydroxy-13-methyl-6,7,8,9,11,12,14,15,16,17-decahydro-cyclopenta[a]phenanthrene-3-oxide; estriol anion: (8R,9S,13S,14S,16R,17R)-16,17-dihydroxy-13-methyl-6,7,8,9,11,12,14,15,16,17-decahydro-cyclopenta[a]phenanthrene-3-oxide; estrone anion: (8R,9S,13S,14S)-17-oxo-13-methyl-7,8,9,11,12,14,15,16-octahydro-6H-cycolpenta-[a]phenanthrene-3-oxide; ethinyl estradiol anion: (8R,9S,13S,14S,17R)-17-hydroxy-17-ethynyl-13-methyl-7,8,9,11,12,14,15,16-octahydro-6H-cyclopenta[a]phenanthrene-3-oxide; ethyl biscoumacetate anion: 2-oxo-3-[2-oxo-2-ethoxy-1-(2-oxo-4-hydroxy-2H-chromen-3-yl)-eth-1-yl]-2H-chromene-4-oxide; ethylidene dicoumarol anion: 2-oxo-3-[1-(2-oxo-4-hydroxy-2H-chromen-3-yl)-eth-1-yl]-2H-chromene-4-oxide; ethyl maltol anion: 2-ethyl-4-oxo-4H-pyran-3-oxide; ethylparaben anion: 4-ethoxycarbonyl-benzene-1-oxide; ethyl vanillin anion: 1-ethyoxy-4-formyl-benzene-1-oxide; eugenol anion: 2-methoxy-4-(prop-2-en-1-yl)-benzene-1-oxide; euparin anion: 2-(prop-1-en-2-yl)-5-(1-oxo-eth-1-yl)-1-benzofuran-6-oxide; eupatorin anion: 2-methoxy-5-(4-oxo-5-hydroxy-6,7-dimethoxy-4H-chromen-2-yl)-benzene-1-oxide or 4-oxo-2-(3-hydroxy-4-methoxy-phen-1-yl)-6,7-dimethoxy-4H-chromene-5-oxide; fenretinide anion: 4-{[1-oxo-3,7-dimethyl-9-(2,6,6-trimethylcyclohex-1-en-1-yl)-non-2,4,6,8-tetraen-1-yl]-amino}-benzene-1-oxide; fisetin anion: 4-oxo-3-hydroxy-2-(3,4-dihydroxy-phen-1-yl)-4H-chromene-7-oxide, 2-hydroxy-4-(4-oxo-3,7-dihydroxy-4H-chromene-2-yl)-benzene-1-oxide, 2-hydroxy-5-(4-oxo-3,7-dihydroxy-4H-chromene-2-yl)-benzene-1-oxide, or 4-oxo-7-hydroxy-2-(3,4-dihydroxy-phen-1-yl)-4H-chromene-3-oxide; flocoumafen anion: 2-oxo-3-{3-[4-(1[4-(trifluoromethyl)-phen-1-yl]-methy}-oxy)-phen-1-yl]-1,2,3,4-tetrahydro-naphthalen-1-yl}-2H-chromene-4-oxide; flopropione anion: 3,5-dihyroxy-4-(1-oxo-prop-1-yl)-benzene-1-oxide or 3,5-dihyroxy-2-(1-oxo-prop-1-yl)-benzene-1-oxide; fluorescein anion: 6'-hydroxy-3-oxo-spiro(2-benzofuran-1,9'-xanthene)-3'-oxide; formononetin anion: 4-oxo-3-(4-methoxy-phen-1-yl)-4H-chromene-7-oxide; fraxetin anion: 2-oxo-7-hydroxy-6-methoxy-2H-chromen-8-oxide or 2-oxo-8-hydroxy-6-methoxy-2H-chromene-7-oxide; fulvestrant anion: (7R,8R,9S,13S,14S,17S)-17-hydroxy-13-methyl-7-19-[(4,4,5,5,5-pentafluoro-pent-1-yl)-sulfinyl]-non-1-yl}-6,7,8,9,11,12,14,15,16,17-decahydro-cyclopenta[a]phenanthrene-3-oxide; fumigatin anion: 3,6-dioxo-2-methoxy-5-methyl-cyclohexa-1,4-diene-1-oxide; fusarubin anion: 3,5-dihydroxy-7-methoxy-3-methyl-6,9-dioxo-1,4-dihydro-benzo[g]isochromene-10-oxide or 3,10-dihydroxy-7-methoxy-3-methyl-6,9-dioxo-1,4-dihydro-benzo[g]isochromene-5-oxide; fustin anion: 2-hydroxy-4-[(2R,3R)-4-oxo-3,7-dihydroxy-2,3-dihydro-4H-chromen-2-yl]-benzene-1-oxide, 2-hydroxy-5-[(2R,3R)-4-oxo-3,7-dihydroxy-2,3-dihydro-4H-chromen-2-yl]-benzene-1- oxide, or (2R,3R)-3-hydroxy-4-oxo-2-(3,4-dihydroxy-phen-1-yl)-2,3-dihydro-4H-chromene-7-oxide; galangin anion: 4-oxo-3,7-dihydroxy-2-phenyl-4H-chromene-5-oxide, 4-oxo-5,7-dihydroxy-2-phenyl-4H-chromene-3-oxide, or 4-oxo-3,5-dihydroxy-2-phenyl-4H-chromene-7-oxide; gallein anion: 1-oxo-3',5',6'-trihydroxyspiro[2-benzofuran-3,9'-xanthene]-4'-oxide or 1-oxo-4',5',6'-trihydroxyspiro[2-benzofuran-3,9'-xanthene]-3'-oxide; gardenin A anion: 4-oxo-2-(3,4,5-trimoxy-phen-1-yl)-6,7,8-trimethoxy-4H-chromene-5-oxide; gardenin B anion: 4-oxo-2-(4-methoxy-phen-1-yl)-6,7,8-trimethoxy-4H-chromene-5-oxide; gardenin C anion: 2,3-dimethoxy-5-(4-oxo-5-hydroxy-6,7,8-trimethoxy-4H-chromen-2-yl)-benzene-1-oxide or 4-oxo-2-(3-hydroxy-4,5-dimethoxy-phen-1-yl)-6,7,8-trimethoxy-4H-chromene-5-oxide; gardenin D anion: 2-methoxy-5-(4-oxo-5-hydroxy-6,7,8-trimethoxy-4H-chromen-2-yl)-benzene-1-oxide or 4-oxo-2-(3-hydroxy-4-methoxy-phen-1-yl)-6,7,8-trimethoxy-4H-chromene-5-oxide; gardenin E anion: 2-methoxy-3-hydroxy-5-(4-oxo-5-hydroxy-6,7,8-trimethoxy-4H-chromen-2-yl)-benzene-1-oxide or 4-oxo-2-(3,5-dihydroxy-4-methoxy-phen-1-yl)-6,7,8-trimethoxy-4H-chromene-5-oxide; genistein anion: 7-hydroxy-4-oxo-3-(4-hydroxy-phen-1-yl)-4H-chromene-5-oxide, 4-(4-oxo-5,7-dihydroxy-4H-chromen-3-yl)-benzene-1-oxide, or 5-hydroxy-4-oxo-3-(4-hydroxy-phen-1-yl)-4H-chromene-7-oxide; gentisin anion: 9-oxo-3-methoxy-7-hydroxy-xanthene-1-oxide or 9-oxo-6-methoxy-8-hydroxy-xanthene-2-oxide; geranylhydroquinone anion: 3-[(2E)-3,7-dimethyl octa-2,6-dien-1-yl]-4-hydroxy-benzene-1-oxide or 2-[(2E)-3,7-dimethylocta-2,6-dien-1-yl]-4-hydroxy-benzene-1-oxide; [6]-gingerol anion: 2-methoxy-4-[(5S)-3-oxo-5-hydroxy-decan-1-yl]-benzene-1-oxide; gossypol anion: 3,5-dihydroxy-4-oxomethyl-6-[1,6,7-trihydroxy-8-oxomethyl-5-(prop-2-yl)-3-methylnapthalen-2-yl]-1-(prop-2-yl)-7-methylnapthalene-2-oxide, 3,8-dihydroxy-1-oxomethyl-7-[1,6,7-trihydroxy-8-oxomethyl-5-(prop-2-yl)-3-methylnapthalen-2-yl]-4-(prop-2-yl)-6-methylnapthalene-2-oxide, or 6,7-dihydroxy-8-oxomethyl-2-[1,6,7-trihydroxy-8-oxomethyl-5-(prop-2-yl)-3-methylnapthalen-2-yl]-5-(prop-2-yl)-3-methylnapthalene-1-oxide; guaiacol anion: 2-methoxy-benzene-1-oxide; para-vinylguaiacol anion: 4-ethenyl-2-methoxy-benzene-1-oxide; hematein anion: 3-oxo-4,6a,10-trihydroxy-6,7-dihydro-indeno[2,1-c] chromene-9-oxide, 3-oxo-4,6a,9-trihydroxy-6,7-dihydro-indeno[2,1-c]chromene-10-oxide, or 3-oxo-6a,9,10-trihydroxy-6,7-dihydro-indeno[2,1-c]chromene-4-oxide; hematoxylin anion: (6aS,11bR)-3,6a,9,10-tetrahydroxy-7,11b-dihydro-6H-indeno[2,1-c]chromene-4-oxide, (6aS,11bR)-3,4,6a, 10-tetrahydroxy-7,11b-dihydro-6H-indeno[2,1-c]chromene-9-oxide, (6aS, 11bR)-3,4,6a,9-tetrahydroxy-7,11b-dihydro-6H-indeno[2,1-c]chromene-10-oxide, or (6aS, 11bR)-4,6a,9,10-tetrahydroxy-7,11b-dihydro-6H-indeno[2,1-c]chromene-3-oxide; herqueinone anion: 3,7-dioxo-4,7a-dihydroxy-5-methoxy-1,8,8,9-tetramethyl-8,9-dihydro-3H-phenaleno[1,2-b]furan-6(7aH)-oxide or 3,7-dioxo-6,7a-dihydroxy-5-methoxy-1,8,8,9-tetramethyl-8,9-dihydro-3H-phenaleno[1,2-b]furan-4(7aH)-oxide; hesperetin anion: (2S)-7-hydroxy-4-oxo-2-(3-hydroxy-4-methoxy-phen-1-yl)-2,3-dihydro-4H-chromene-5-oxide, 2-methoxy-5-[(2S)-4-oxo-5,7-dihydroxy-2,3-dihydro-4H-chromen-2-yl]-benzene-1-oxide, or (2S)-5-hydroxy-4-oxo-2-(3-hydroxy-4-methoxy-phen-1-yl)-2,3-dihydro-4H-chromene-7-oxide; hexestrol anion: 4-[4-(4-hydroxy-phen-1-yl]-hex-3-A-benzene-1-oxide; 4-hexylresorcinol anion: 3-hydroxy-6-hexyl-benzene-1-oxide or 3-hydroxy-4-hexyl-benzene-1-oxide; homoeriodictyol anion: (2S)-4-oxo-7-hydroxy-2-(4-hydroxy-3-methoxy-phen-1-yl)-2,3-dihydro-4H-chromene-5-oxide, 2-methoxy-4-[4-oxo-5,7-dihydroxy-2,3-dihydro-4H-chromen-2-A-benzene-1-oxide, or (2S)-4-oxo-5-hydroxy-2-(4-hydroxy-3-methoxy-phen-1-yl)-2,3-dihydro-4H-chromene-7-oxide; homosalate anion: 2-{[(3,3,5-trimethylcyclohex-1-yl)-oxy]-carbonyl}-benzene-1-oxide; honokiol anion: 2-[4-hydroxy-3-(prop-2-enyl)-phen-1-yl]-4-(prop-2-enyl)-benzene-1-oxide or 4-[2-hydroxy-5-(prop-2-enyl)-phen-1-yl]-2-(prop-2-enyl)-benzene-1-oxide; 4-O-methylhonokiol anion: 2-[4-methoxy-3-(prop-2-enyl)-phen-1-yl]-4-(prop-2-enyl)-benzene-1-oxide; hydroxytyrosol anion: 2-hydroxy-4-(2-hydroxyeth-1-yl)-benzene-1-oxide or 2-hydroxy-5-(2-hydroxyeth-1-yl)-benzene-1-oxide; hymecromone anion: 7-oxo-4-methyl-7H-chromen-2-oxide or 2-oxo-4-methyl-2H-chromene-7-oxide; ilimaquinone anion: 3,6-dioxo-2-{[(1R,2S,4aS,8aS)-1,2,4-trimethyl-5-methylidene-3,4,6,7,8,8a-hexahy dro-2H-naphthal en-1-yl]-methyl}-4-methoxy-cyclohexa-1,4-diene-1-oxide; irigenin anion: 4-oxo-7-hydroxy-6-methoxy-3-(3-hydroxy-4,5-dimethoxy-phen-1-yl)-4H-chromene-5-oxide, 2,3-dimethoxy-5-(4-oxo-5,7-dihydroxy-6-methoxy-4H-chromen-3-yl)-benzene-1-oxide, or 4-oxo-5-hydroxy-6-methoxy-3-(3-hydroxy-4,5-dimethoxy-phen-1-yl)-4H-chromene-7-oxide; isoestradiol anion: (8S,9S,13S,14S,17S)-17-hydroxy-13-methyl-6,7,8,9,11,12,14,15,16,17-decahydro-cyclopenta[a]phenanthrene-3-oxide; 8-isoestrone anion: (8S,9S,13S,14S)-17-oxo-13-methyl-7,8,9,11,12,14,15,16-octahydro-6H-cyclopenta[a]phenanthrene-3-oxide; isoeugenol anion: 2-methoxy-4-(prop-1-enyl)-benzene-1-oxide; isomaltol anion: 2-acetyl-furan-3-oxide; ivacaftor anion: 3-{[(4-oxo-1,4-dihydro-quinolin-3-yl)-carbonyl]-amino}-4,6-bis(2-methylprop-2-yl)-benzene-1-oxide; javanicin anion: 5,8-dioxo-4-hydroxy-3-methoxy-7-methyl-6-(2-oxo-propyl)-naphthalene-1-oxide or 5,8-dioxo-4-hydroxy-2-methoxy-6-methyl-7-(2-oxo-propyl)-naphthalene-1-oxide; juglone anion: 5,8-naphthalene-1-oxide; kaempferol anion: 4-oxo-3,7-dihydroxy-2-(4-hydroxy-phen-1-yl)-4H-chromene-5-oxide, 4-oxo-3,5-dihydroxy-2-(4-hydroxy-phen-1-yl)-4H-chromene-7-oxide, 4-(4-oxo-3,5,7-trihydroxy-4H-chromen-2-yl)-benzene-1-oxide, or 4-oxo-5,7-dihydroxy-2-(4-hydroxy-phen-1-yl)-4H-chromene-3-oxide; dihydrokaempferol anion: 4-oxo-3,5-dihydroxy-2-(4-hydroxy-phen-1-yl)-2,3-dihydro-4H-chromene-7-oxide, 4-(4-oxo-3,5,7-trihydroxy-2,3-dihydro-4H-chromen-2-yl)-benzene-1-oxide, or 4-oxo-3,7-dihydroxy-2-(4-hydroxy-phen-1-yl)-2,3-dihydro-4H-chromene-5-oxide; 4'-O-methylkaempferol anion: 4-oxo-3,7-dihydroxy-2-(4-methoxy-phen-1-yl)-4H-chromene-5-oxide, 4-oxo-3,5-dihydroxy-2-(4-methoxy-phen-1-yl)-4H-chromene-7-oxide, or 4-oxo-5,7-dihydroxy-2-(4-methoxy-phen-1-yl)-4H-chromene-3-oxide; dihydrokaempferi de anion: 4-oxo-3,5-dihydroxy-2-(4-methoxy-phen-1-yl)-2,3-dihydro-4H-chromene-7-oxide or 4-oxo-3,7-dihydroxy-2-(4-methoxy-phen-1-yl)-2,3-dihydro-4H-chromene-5-oxide; alpha-kosin anion: 5-hydroxy-3-methoxy-4-(1-oxo-2-methylprop-1-yl)-6-{[2,6-dihydroxy-4-methoxy-3-(1-oxo-2-methylprop-1-yl)-5-methylphen-1-yl]-methyl}-2-methylbenzene-1-oxideor 5-hydroxy-3-methoxy-2-(1-oxo-2-methylprop-1-yl)-6-{[2,6-dihydroxy-4-methoxy-3-(1-oxo-2-methylprop-1-yl)-5-methylphen-1-A-methyl}-4-methylbenzene-1-oxide; beta-kosin anion: 3,5-dihydroxy-2-(1-oxo-2-methylprop-1-yl)-6-{[2-hydroxy-4,6-dimethoxy-5-(1-oxo-2-methylprop-1-yl)-3-methylphen-1-yl]-methyl}-4-methylbenzene-1-oxide, 3,5-dihydroxy-4-(1-oxo-2-methylprop-1-yl)-2-{[2-hydroxy-4,6-dimethoxy-5-(1-oxo-2-methylprop-1-yl)-3-methylphen-1-yl]-methyl}-6-methylbenzene-1-oxide, 3,5-dimethoxy-4-(1-oxo-2-methylprop-1-yl)-2-{[2,4,6-trihydroxy-3-(1-oxo-2-methylprop-1-yl)-5-methylphen-1- yl]-methyl}-6-methylbenzene-1-oxide, or 3,5-dihydroxy-2-(1-oxo-2-methylprop-1-yl(-4-{[2-hydroxy-4,6-dimethoxy-5-(1-oxo-2-methylprop-1-yl)-3-methylphen-1-yl]-methyl}-6-methylbenzene-1-oxide; lapachol anion: 1,4-dioxo-3-(3-methyl-but-2-en-1-yl)-naphthal ene-2-oxide; lawsone anion: 1,4-dioxo-naphthalene-2-oxide; leucocyanidin anion: 2-(3,4-dihydroxy-phen-1-yl)-3,4,5-trihydroxy-3,4-dihydro-2H-chromene-7-oxide, 2-hydroxy-4-(3,4,5,7-tetrahydroxy-3,4-dihydro-2H-chromen-2-yl)-benzene-1-oxide, 2-hydroxy-5-(3,4,5,7-tetrahydroxy-3,4-dihydro-2H-chromen-2-yl)-benzene-1-oxide, or 2-(3,4-dihydroxy-phen-1-yl)-3,4,7-trihydroxy-3,4-dihydro-2H-chromene-5-oxide; licochalcone A anion: 3-methoxy-443-oxo-3-(4-hydroxyphen-1-yl)-prop-1-en-1-yl]-6-(2-methylbut-3-en-2-yl)-benzene-1-oxide or 4-{1-oxo-3-[4-hydroxy-2-methoxy-5-(2-methylbut-3-en-2-yl)-phen-1-yl]-prop-2-en-1-yl}-benzene-1-oxide; licochalcone B anion: 3-methoxy-2-hydroxy-4-[3-oxo-3-(4-hydroxyphen-1-yl)-prop-1-en-1-yl]-benzene-1-oxide, 6-methoxy-2-hydroxy-5-[3-oxo-3-(4-hydroxyphen-1-yl)-prop-1-en-1-yl]-benzene-1-oxide, or 4-[1-oxo-3-(2-methoxy-3,4-dihydroxyphen-1-yl)-prop-2-en-1-yl]-benzene-1-oxide; licochalcone C anion: 3-methoxy-4-[3-oxo-3-(4-hydroxyphen-1-yl)-prop-1-en-1-yl]-2-(3-methylbut-2-en-1-yl)-benzene-1-oxide or 4-{1-oxo-3,4-hydroxy-2-methoxy-3-(3-methylbut-2-en-1-yl)-phen-1-yl]-prop-2-en-1-yl}-benzene-1-oxide; licochalcone D anion: 3-methoxy-2-hydroxy-4-{3-oxo-3-[4-hydroxy-3-(3-methylbut-2-en-1-yl)-phen-1-yl]-prop-1-en-1-yl}-benzene-1-oxide, 6-methoxy-2-hydroxy-5-{3-oxo-3-[4-hydroxy-3-(3-methylbut-2-en-1-yl)-phen-1-yl]-prop-1-en-1-yl}-benzene-1-oxide, or 2-(3-methylbut-2-en-1-yl)-4-[1-oxo-3-(2-methoxy-3,4-dihydroxyphen-1-yl)-prop-2-en-1-yl]-benzene-1-oxide; licochalcone E anion: 3-methoxy-443-oxo-3-(4-hydroxyphen-1-yl)-prop-1-en-1-yl]-6-(3-methylbut-3-en-2-yl)-benzene-1-oxide or 4-{1-oxo-3-[4-hydroxy-2-methoxy-5-(3-methylbut-3-en-2-yl)-phen-1-yl]-prop-2-en-1-yl}-benzene-1-oxide; luteolin anion: 4-oxo-5-hydroxy-2-(3,4-dihydroxy-phen-1-yl)-4H-chromene-7-oxide, 2-hydroxy-4-(4-oxo-5,7-dihydroxy-4H-chromen-2-yl)-benzene-1-oxide, 2-hydroxy-5-(4-oxo-5,7-dihydroxy-4H-chromen-2-yl)-benzene-1-oxide, or 4-oxo-7-hydroxy-2-(3,4-dihydroxy-phen-1-yl)-4H-chromene-5-oxide; magnolol anion: 4-(prop-2-en-1-yl)-2-[5-(prop-2-en-1-yl)-2-hydroxy-phen-1-yl]-benzene-1-oxide; maltol anion: 4-oxo-2-methyl-4H-pyran-3-oxide; mangostin anion: 9-oxo-2-methoxy-3,8-dihydroxy-1,7-bis(3-methyl-but-2-en-1-yl)-xanthene-6-oxide, 9-oxo-2-methoxy-3,6-dihydroxy-1,7-bis(3-methyl-but-2-en-1-yl)-xanthene-8-oxide, or 9-oxo-2-methoxy-6,8-dihydroxy-1,7-bis(3-methyl-but-2-en-1-yl)-xanthene-3-oxide; beta-mangostin anion: 9-oxo-2,6-dimethoxy-3-hydroxy-1,7-bis(3-methyl-but-2-en-1-yl)-xanthene-8-oxide or 9-oxo-2,6-dimethoxy-8-hydroxy-1,7-bis(3-methyl-but-2-en-1-yl)-xanthene-3-oxide; gamma-mangostin anion: 9-oxo-2,6,8-trihydroxy-1,7-bis(3-methyl-but-2-en-1-yl)-xanthene-3-oxide, 9-oxo-2,3,8-trihydroxy-1,7-bis(3-methyl-but-2-en-1-yl)-xanthene-6-oxide, 9-oxo-2,3,6-trihydroxy-1,7-bis(3-methyl-but-2-en-1-yl)-xanthene-8-oxide, or 9-oxo-3,6,8-trihydroxy-1,7-bis(3-methyl-but-2-en-1-yl)-xanthene-2-oxide; 6-deoxy-gamma mangostin anion: 9-oxo-2,8-dihydroxy-1,7-bis(3-methyl-but-2-en-1-yl)-xanthene-6-oxide, 9-oxo-2,6-dihydroxy-1,7-bis(3-methyl-but-2-en-1-yl)-xanthene-8-oxide, or 9-oxo-6,8-dihydroxy-1,7-bis(3-methyl-but-2-en-1-yl)-xanthene-2-oxide; 3,6-dimethylmangostin anion: 9-oxo-2,3,6-trimethoxy-1,7-bis(3-methyl-but-2-en-1-yl)-xanthene-8-oxide; medicagol anion: 6-oxo-(1,3)dioxolo(5,6)[1]benzofuro[3,2-c]chromen-3(6H)-oxide; medicarpin anion: 9-methoxy-6a,11a-dihydro-6H-[1]benzofuro[3,2-c]chromen-3-oxide; menadiol anion: 4-hydroxy-3-methyl-naphthalene-1-oxide or 4-hydroxy-2-methyl-naphthalene-1-oxide; methestrol anion: 4-[4-(4-hydroxy-3-methyl-phen-1-yl)-hexan-3-yl]-2-methyl-benzene-1-oxide; 3-methoxy-4-hydroxyphenylglycol anion: 2-methoxy-4-(1,2-dihydroxyethyl)-benzene-1-oxide; methylparaben anion: 4-methoxycarbonyl-benzene-1-oxide; mexenone anion: 3-methoxy-6-[(4-methylphen-1-yl)-carbonyl]-benzene-1-oxide; monobenzone anion: 4-(benzyloxy)-benzene-1-oxide; morin anion: 4-oxo-3,7-dihydroxy-2-(2,4-dihydroxy-phen-1-yl)-4H-chromene-5-oxide, 4-oxo-3,5-dihydroxy-2-(2,4-dihydroxy-phen-1-yl)-4H-chromene-7-oxide, 3-hydroxy-4-(4-oxo-3,5,7-trihydroxy-4H-chromen-2-yl)-benzene-1-oxide, 3-hydroxy-6-(4-oxo-3,5,7-trihydroxy-4H-chromen-2-yl)-benzene-1-oxide, or 4-oxo-5,7-dihydroxy-2-(2,4-dihydroxy-phen-1-yl)-4H-chromene-3-oxide; moxestrol anion: (8R,9S,11S,13S,14S,17R)-17-hydroxy-17-ethynyl-11-methoxy-13-methyl-7,8,9,11,12,14,15,16-octahydro-6H-cyclopenta[a]phenanthrene-3-oxide; myricetin anion: 4-oxo-3,7-dihydroxy-2-(3,4,5-trihydroxy-phen-1-yl)-4H-chromene-5-oxide, 4-oxo-3,5-dihydroxy-2-(3,4,5-trihydroxy-phen-1-yl)-4H-chromene-7-oxide, 2,6-dihydroxy-4-(4-oxo-3,5,7-trihydroxy-4H-chromen-2-yl)-benzene-1-oxide, 2,3-dihydroxy-5-(4-oxo-3,5,7-trihydroxy-4H-chromen-2-yl)-benzene-1-oxide, or 4-oxo-5,7-dihydroxy-2-(3,4,5-trihydroxy-phen-1-yl)-4H-chromene-3-oxide; nabilone anion: 9-oxo-6,6-dimethyl-3-(2-methyloctan-2-yl)-6,6a,7,8,10,10a-hexahydro-9H-benzo[c]chromene-1-oxide; 2-naphthol anion: naphthalene-2-oxide; alpha-naphtholphthalein anion: 4-(3-oxo-1-(4-hydroxy-naphthalen-1-yl)-2-benzofuran-1-yl]-napthalene-1-oxide; naphthoresorcinol anion: 4-hydroxy-napthalene-2-oxide or 3-hydroxy-napthalene-1-oxide; naringenin anion: 4-oxo-5-hydroxy-2-(4-hydroxyphen-1-yl)-2,3-dihydro-4H-chromene-7-oxide, 4-(4-oxo-5,7-dihydroxy-2,3-dihydro-4H-chromen-2-yl)-benzene-1-oxide, or 4-oxo-7-hydroxy-2-(4-hydroxyphen-1-yl)-2,3-dihydro-4H-chromene-5-oxide; nimbi ol anion: 9-oxo-1,1,4 a,7-tetramethyl-2,3,4,4a,10,10a-hexahydro-1H-phenanthrene-6-oxide; nordihydroguaiaretic acid anion: 2-hydroxy-5-[4-(3,4-dihydroxy-phen-1-yl)-2,3-dimethyl-but-1-yl]-benzene-1-oxide or 2-hydroxy-4-[4-(3,4-dihydroxy-phen-1-yl)-2,3-dimethyl-but-1-yl]-benzene-1-oxide; heminordihydroguaiaretic acid anion: 2-hydroxy-5-[4-(4-hydroxy-3-methoxy-phen-1-yl)-2,3-dimethyl-but-1-yl]-benzene-1-oxide, 2-methoxy-4-[4-(3,4-dihydroxy-phen-1-yl)-2,3-dimethyl-but-1-yl]-benzene-1-oxide, or 2-hydroxy-4-[4-(4-hydroxy-3-methoxy-phen-1-yl)-2,3-dimethyl-but-1-yl]-benzene-1-oxide; octabenzone anion: 5-octanoxy-2-(phenyl-carbonyl)-benzene-1-oxide; oleocanthal anion: 4-(2-{[1-oxo-4-carbonyl-3-(2-oxo-eth-1-yl)-hex-4-en-1-yl]-oxy}-eth-1-yl)-benzene-1-oxide; oroxylin A anion: 4-oxo-6-methoxy-5-hydroxy-2-phenyl-4H-chromene-7-oxide or 4-oxo-6-methoxy-7-hydroxy-2-phenyl-4H-chromene-5-oxide; orthocaine anion: 2-amino-4-methoxycarbonyl-benzene-1-oxide; gamma-oryzanol anion: 2-methoxy-4-(3-oxo-3-{[9,10-methylene-17-(6-methylhept-5-en-2-yl)-4,4,13,14-tetramethyl-1,2,3,5,6,7,8,11,12,15,16,17-dodecahydro-4H-cyclopenta[a]phenanthren-3-yl]-oxy}-prop-1-en-1-yl)-benzene-1-oxide; oryzanol C anion: 2-methoxy-4-(3-oxo-34[9,10-methylene-17-(5-methylidene-6-methylhept-2-yl)-4,4,13,14-tetramethyl-1,2,3,5,6,7,8,11,12,15,16,17-dodecahydro-4H-cyclopenta[a]phenanthren-3-A-oxy-prop-1-en-1-yl)-benzene-1-oxide; osalmid anion: 4-{[(2-hydroxyphen-1-yl)-carbonyl]-amino}-benzene-1-oxide or 2-{[(4-hydroxyphen-1-yl)-amino]-carbonyl}-benzene-1-oxide; ostruthin anion: 2-oxo-6-[(2E)-3,7-dimethyl-octa-2,6-dien-1-yl)-2H-chromene-7- oxide; oxybenzone anion: 3-methoxy-6-(phenyl-carbonyl)-benzene-1-oxide; oxyphenbutazone anion: 4-(3,5-dioxo-4-butyl-2-phenyl-pyrazolidin-1-yl)-benzene-1-oxide; paroxypropione anion: 4-(1-oxo-prop-1-yl)-benzene-1-oxide; parvaquone anion: 3,4-dioxo-2-cyclohexyl-naphthalene-1-oxide; pectolinarigenin anion: 4-oxo-6-methoxy-5-hydroxy-2-(4-methoxy-phen-1-yl)-4H-chromene-7-oxide or 4-oxo-6-methoxy-7-hydroxy-2-(4-methoxy-phen-1-yl)-4H-chromene-5-oxide; alpha-peltatin anion: (5aR,8aR,9R)-8-oxo-9-(3,5-dimethoxy-4-hydroxyphen-1-yl)-5a,6,8a,9-tetrahydro-5H-[2]benzofuro[5,6-f][1,3]benzodioxol-4-oxide; beta-peltatin anion: (5aR,8aR,9R)-8-oxo-9-(3,4,5-trimethoxy-phen-1-yl)-5a,6,8a,9-tetrahydro-5H-[2]benzofuro[5,6-f][1,3]benzodioxol-4-oxide; para-tert-pentyl-phenol anion: 4-(2-methyl-but-2-yl)-benzene-1-oxide; perezone anion: 3,6-dioxo-2-(6-methylhept-5-en-2-yl)-5-methylcyclohexa-1,4-diene-1-oxide; phaseolin anion: 3,3-dimethyl-6b,12b-dihydro-3H,7H-furo[3,2-c:5,4-n]dichromen-10-oxide; phenolphthalol anion: 44[2-(hydroxymethyl)-phen-1-yl]-(4-hydroxyphen-1-yl)-methyl}-benzene-1-oxide; phenprocoumon anion: 2-oxo-3-(1-phenyl-prop-1-yl)-2H-chromene-4-oxide; phloretin anion: 3,5-dihydroxy-4-[1-oxo-3-(4-hydroxyphen-1-yl)-prop-1-yl]-benzene-1-oxide, 4-[3-oxo-3-(2,4,6-trihydroxyphen-1-yl)-prop-1-yl]-benzene-1-oxide, or 3,5-dihydroxy-2-[1-oxo-3-(4-hydroxy-phen-1-yl)-prop-1-yl]-benzene-1-oxide; phthiocol anion: 3,4-dioxo-2-methyl-naphthalene-1-oxide; pinosylvin anion: 3-hydroxy-5-[(E)-2-phenyl-ethen-1-yl]-benzene-1-oxide; pinosylvin monomethyl ether anion: 3-methoxy-5-[(E)-2-phenyl-ethen-1-yl]-benzene-1-oxide; plumbagin anion: 5,8-dioxo-6-methyl-naphthalene-1-oxide; pratensein anion: 4-oxo-5-hydroxy-3-(3-hydroxy-4-methoxy-phen-1-yl)-4H-chromen-7-oxide, 2-methoxy-5-(4-oxo-5,7-dihydroxy-4H-chromen-3-yl)-benzene-1-oxide, or 4-oxo-7-hydroxy-3-(3-hydroxy-4-methoxy-phen-1-yl)-4H-chromen-5-oxide; probucol anion: 2,6-di(2-methylprop-2-yl)-4-[(24[4-hydroxy-3,5-di(2-methylprop-2-yl)-phen-1-yl]-sulfanyl-propan-2-yl)-sulfanyl]-benzene-1-oxide; propofol anion: 2,6-di(prop-2-yl)-benzene-1-oxide; propyl gallate anion: 2,6-dihydroxy-4-(propoxy-carbonyl)-benzene-1-oxide or 2,3-dihydroxy-5-(propoxy-carbonyl)-benzene-1-oxide; propylparab en anion: 4-(propoxy-carbonyl)-benzene-1-oxide; protocatechualdehyde anion: 2-hydroxy-5-formyl-benzene-1-oxide or 2-hydroxy-4-formyl-benzene-1-oxide; prunetin anion: 4-(4-oxo-7-methoxy-5-hydroxy-4H-chromen-3-yl)-benzene-1-oxide or 4-oxo-7-methoxy-3-(4-hydroxyphen-1-yl)-4H-chromen-5-oxide; pseudobaptigenin anion: 4-oxo-3-(1,3-benzodioxol-5-yl)-4H-chromene-7-oxide; purpurin anion: 1,4-dihydroxy-9,10-dioxo-anthracene-2-oxide, 3,4-dihydroxy-9,10-dioxo-anthracene-1-oxide, or 2,4-dihydroxy-9,10-dioxo-anthracene-1-oxide; purpurin 1-methyl ether anion: 9,10-dioxo-1-methoxy-4-hydroxy-anthracene-2-oxide or 9,10-dioxo-4-methoxy-3-hydroxy-anthracene-1-oxide; purpurin 2-methyl ether anion: 4-hydroxy-3-methoxy-9,10-dioxo-anthracene-1-oxide or 4-hydroxy-2-methoxy-9,10-dioxo-anthracene-1-oxide; purpurin 2,4-dimethyl ether anion: 2,4-dimethoxy-9,10-dioxo-anthracene-1-oxide; anthrapurpurin anion: 9,10-dioxo-1,7-dihydroxy-anthracene-2-oxide, 9,10-dioxo-7,8-dihydroxy-anthracene-2-oxide, or 9,10-dioxo-2,7-dihydroxy-anthracene-1-oxide; flavopurpurin anion: 9,10-dioxo-1,6-dihydroxy-anthracene-2-oxide, 9,10-dioxo-5,6-dihydroxy-anthracene-2-oxide, or 9,10-dioxo-2,6-dihydroxy-anthracene-1-oxide; purpurogallin anion: 5-oxo-2,4,6-trihydroxy-benzo[7]annulen-2-oxide, 5-oxo-2,3,6-trihydroxy-benzo[7]annulen-4-oxide, 5-oxo-2,3,4-trihydroxy-benzo[7]annulen-6-oxide, or 5-oxo-3,4,6-trihydroxy-benzo[7]annulen-2-oxide; quercetagetin anion: 4-oxo-3,6,7-trihydroxy-2-(3,4-dihydroxy-phen-1-yl)-4H-chromene-5-oxide, 4-oxo-3,5,7-trihydroxy-2-(3,4-dihydroxy-phen-1-yl)-4H-chromene-6-oxide, 4-oxo-3,5,6-trihydroxy-2-(3,4-dihydroxy-phen-1-yl)-4H-chromene-7-oxide, 2-hydroxy-4-(4-oxo-3,5,6,7-tetrahydroxy-4H-chromen-2-yl)-benzene-1-oxide, 2-hydroxy-5-(4-oxo-3,5,6,7-tetrahydroxy-4H-chromen-2-yl)-benzene-1-oxide, or 4-oxo-5,6,7-trihydroxy-2-(3,4-dihydroxy-phen-1-yl)-4H-chromene-3-oxide; quercetin anion: 4-oxo-3,7-dihydroxy-2-(3,4-dihydroxy-phen-1-yl)-4H-chromene-5-oxide, 4-oxo-3,5-dihydroxy-2-(3,4-dihydroxy-phen-1-yl)-4H-chromene-7-oxide, 2-hydroxy-4-(4-oxo-3,5,7-trihydroxy-4H-chromene-2-yl)-benzene-1-oxide, 2-hydroxy-5-(4-oxo-3,5,7-trihydroxy-4H-chromene-2-yl)-benzene-1-oxide, or 4-oxo-5,7-dihydroxy-2-(3,4-dihydroxy-phen-1-yl)-4H-chromene-3-oxide; quinalizarin anion: 9,10-dioxo-1,5,8-trihydroxy-anthracene-2-oxide, 9,10-dioxo-4,5,6-trihydroxy-anthracene-1-oxide, 9,10-dioxo-4,7,8-trihydroxy-anthracene-1-oxide, or 9,10-dioxo-2,5,8-trihydroxy-anthracene-1-oxide; resacetophenone anion: 3-hydroxy-6-(1-oxo-eth-1-yl)-benzene-1-oxide or 3-hydroxy-4-(1-oxo-eth-1-yl)-benzene-1-oxide; beta-resorcylaldehyde anion: 3-hydroxy-6-formyl-benzene-1-oxide or 3-hydroxy-4-formyl-benzene-1-oxide; resveratrol anion: 3-hydroxy-5-[(E)-2-(4-hydroxyphen-1-yl)-ethen-1-yl]-benzene-1-oxide or 4-[(E)-2-(3,5-hydroxy-phen-1-yl)-ethen-1-yl]-benzene-1-oxide; dihydroresveratrol anion: 3-hydroxy-5-[2-(4-hydroxyphen-1-yl)-eth-1-yl]-benzene-1-oxide or 4-[2-(3,5-dihydroxy-phen-1-yl)-eth-1-yl]-benzene-1-oxide; rhamnetin anion: 4-oxo-7-methoxy-3-hydroxy-2-(3,4-hydroxy-phen-1-yl)-4H-chromene-5-oxide, 2-hydroxy-4-(4-oxo-7-methoxy-3,5-dihydroxy-4H-chromen-2-yl)-benzene-1-oxide, 2-hydroxy-5-(4-oxo-7-methoxy-3,5-dihydroxy-4H-chromen-2-yl)-benzene-1-oxide, or 4-oxo-7-methoxy-5-hydroxy-2-(3,4-hydroxy-phen-1-yl)-4H-chromene-3-oxide; linomide anion: 2-oxo-3-[(N-phenyl-N-methyl-amino)-carbonyl]-N-methyl-1,2-dihydroquinoline-4-oxide; rottlerin anion: 5-hydroxy-8-(1-oxo-3-phenyl-prop-2-en-1-yl)-6-[(2,4,6-trihydroxy-3-acetyl-5-methyl-phen-1-yl)-methyl]-2,2-dimethyl-2H-chromene-7-oxide, 3,5-dihydroxy-6-{[5,7-dihydroxy-8-(1-oxo-3-phenyl-prop-2-en-1-yl)-2,2-dimethyl-2H-chromen-6-yl]-methyl}-2-acetyl-4-methylbenzene-1-oxide, 3,5-dihydroxy-2-[5,7-dihydroxy-8-(1-oxo-3-phenyl-prop-2-en-1-yl)-2,2-dimethyl-2H-chromen-6-yl]-methyl I-4-acetyl-6-methylbenzene-1-oxide, 3,5-dihydroxy-4-[5,7-dihydroxy-8-(1-oxo-3-phenyl-prop-2-en-1-yl)-2,2-dimethyl-2H-chromen-6-yl]-methyl I-2-acetyl-6-methylbenzene-1-oxide, or 7-hydroxy-8-(1-oxo-3-phenyl-prop-2-en-1-yl)-6-[(2,4,6-trihydroxy-3-acetyl-5-methyl-phen-1-yl)-methyl]-2,2-dimethyl-2H-chromene-5-oxide; tetrahydrorottlerin anion: 5-hydroxy-8-(1-oxo-3-phenyl-prop-1-yl)-6-[(2,4,6-trihydroxy-3-acetyl-5-methyl-phen-1-yl)-methyl]-2,2-dimethyl-3,4-dihydro-2H-chromene-7-oxide, 3,5-dihydroxy-6-{[5,7-dihydroxy-8-(1-oxo-3-phenyl-prop-1-yl)-2,2-dimethyl-3,4-dihydro-2H-chromen-6-yl]-methyl}-2-acetyl-4-methylbenzene-1-oxide, 3,5-dihydroxy-2-{[5,7-dihydroxy-8-(1-oxo-3-phenyl-prop-1-yl)-2,2-dimethyl-3,4-dihydro-2H-chromen-6-yl]-methyl}-4-acetyl-6-methylbenzene-1-oxide, 3,5-dihydroxy-4-{[5,7-dihydroxy-8-(1-oxo-3-phenyl-prop-1-yl)-2,2-dimethyl-3,4-dihydro-2H-chromen-6-yl]-methyl}-2-acetyl-6-methylbenzene-1-oxide, or 7-hydroxy-8-(1-oxo-3-phenyl-prop-1-yl)-6-[(2,4,6-trihydroxy-3-acetyl-5-methyl-phen-1-yl)-methyl]-2,2-dimethyl-3,4-dihydro-2H-chromene-5-oxide; rottlerin 5,7-dimethyl ether anion: 3,5-dihydroxy-2-{[5,7-dimethoxy-8-(1-oxo-3-phenyl-prop-1-yl)-2,2- dimethyl-3,4-dihydro-2H-chromen-6-yl]-methyl}-4-acetyl-6-methylbenzene-1-oxide, 3,5-dihydroxy-4-{[5,7-dimethoxy-8-(1-oxo-3-phenyl-prop-1-yl)-2,2-dimethyl-3,4-dihydro-2H-chromen-6-yl]-methyl}-2-acetyl-6-methylbenzene-1-oxide, or 3,5-dihydroxy-6-{[5,7-dimethoxy-8-(1-oxo-3-phenyl-prop-1-yl)-2,2-dimethyl-3,4-dihydro-2H-chromen-6-yl]-methyl}-2-acetyl-4-methylbenzene-1-oxide; rubiadin anion: 9,10-dioxo-4-hydroxy-3-methyl-anthracene-2-oxide or 9,10-dioxo-3-hydroxy-2-methyl-anthracene-1-oxide; salicyl alcohol anion: 2-(hydroxymethyl)-benzene-1-oxide; salicylaldehyde anion: 2-formyl-benzene-1-oxide; salicylanilide anion: 2-[(phenylamino)-carbonyl]-benzene-1-oxide; scopoletin anion: 2-oxo-6-methoxy-2H-chromene-7-oxide; scutellarein anion: 4-oxo-5,7-dihydroxy-2-(4-hydroxyphen-1-yl)-4H-chromen-6-oxide, 4-oxo-5,6-dihydroxy-2-(4-hydroxyphen-1-yl)-4H-chromen-7-oxide, 4-(4-oxo-5,6,7-trihydroxy-4H-chromen-2-yl)-benzene-1-oxide, or 4-oxo-6,7-dihydroxy-2-(4-hydroxyphen-1-yl)-4H-chromen-5-oxide; siccanin anion: 8,12,16,16-tetramethyl-3,11-dioxa-pentacyclo [10.7.1.01$^{1.15}$.0$^{4.20}$.0$^{5.10}$]-icosa-5,7,9-trien-6-oxide; silybin A anion: (2R,3R)-3,5-dihydroxy-4-oxo-2-[(2R,3R)-3-(4-hydroxy-3-methoxy-phen-1-yl)-2-(hydroxymethyl)-2,3-dihydro-1,4-benzodioxin-6-yl]-2,3-dihydro-4H-chromene-7-oxide, 2-methoxy-4-{(2R,3R)-2-(hydroxymethyl)-6-[(2R, 3R)-4-oxo-3,5,7-trihydroxy-2,3-dihydro-4H-chromen-2-yl]-2,3-dihydro-1,4-benzodioxin-3-yl}-benzene-1-oxide, or (2R,3R)-3,7-dihydroxy-4-oxo-2-[(2R,3R)-3-(4-hydroxy-3-methoxy-phen-1-yl)-2-(hydroxymethyl)-2,3-dihydro-1,4-benzodioxin-6-yl]-2,3-dihydro-4H-chromene-5-oxide; silybin B anion: (2R,3R)-3,5-dihydroxy-4-oxo-2-[(2S,3S)-3-(4-hydroxy-3-methoxy-phen-1-yl)-2-(hydroxymethyl)-2,3-dihydro-1,4-benzodioxin-6-yl]-2,3-dihydro-4H-chromene-7-oxide, 2-methoxy-4-{(2S,3S)-2-(hydroxymethyl)-6-[(2R,3R)-4-oxo-3,5,7-trihydroxy-2,3-dihydro-4H-chromen-2-yl]-2,3-dihydro-1,4-benzodioxin-3-yl}-benzene-1-oxide, or (2R,3R)-3,7-dihydroxy-4-oxo-2-[(2S,3S)-3-(4-hydroxy-3-methoxy-phen-1-yl)-2-(hydroxymethyl)-2,3-dihydro-1,4-benzodioxin-6-yl]-2,3-dihydro-4H-chromene-5-oxide; isosilybin A anion: (2R,3R)-3,5-dihydroxy-4-oxo-2-[(2R,3R)-3-(4-hydroxy-3-methoxy-phen-1-yl)-2-(hydroxymethyl)-2,3-dihydro-1,4-benzodioxin-7-yl]-2,3-dihydro-4H-chromene-7-oxide, 2-methoxy-4-{(2R, 3R)-2-(hydroxymethyl)-7-[(2R,3R)-4-oxo-3,5,7-trihydroxy-2,3-dihydro-4H-chromen-2-yl]-2,3-dihydro-1,4-benzodioxin-3-yl}-benzene-1-oxide, or (2R, 3R)-3,7-dihydroxy-4-oxo-2-[(2R,3R)-3-(4-hydroxy-3-methoxy-phen-1-yl)-2-(hydroxymethyl)-2,3-dihydro-1,4-benzodioxin-7-yl]-2,3-dihydro-4H-chromene-5-oxide; isosilybin B anion: (2R,3R)-3,5-dihydroxy-4-oxo-2-[(2S, 3S)-3-(4-hydroxy-3-methoxy-phen-1-yl)-2-(hydroxymethyl)-2,3-dihydro-1,4-benzodioxin-7-yl]-2,3-dihydro-4H-chromene-7-oxide, 2-methoxy-4-{(2S,3S)-2-(hydroxymethyl)-7-[(2R,3R)-4-oxo-3,5,7-trihydroxy-2,3-dihydro-4H-chromen-2-yl]-2,3-dihydro-1,4-benzodioxin-3-yl 1-benzene-1-oxide, or (2R,3R)-3,7-dihydroxy-4-oxo-2-[(2S,3S)-3-(4-hydroxy-3-methoxy-phen-1-yl)-2-(hydroxymethyl)-2,3-dihydro-1,4-benzodioxin-7-yl]-2,3-dihydro-4H-chromene-5-oxide; sparassol anion: 3-methoxy-6-methoxycarbonyl-5-methylbenzene-1-oxide; strobilurin F anion: 2-[(3-methylbut-2-en-1-yl)-oxy]-5-[(2E, 3Z,5E)-6-methoxy-5-(methoxycarbonyl)-4-methylhexa-1,3,5-trienyl]-benzene-1-oxide; sulfuretin anion: 2-hydroxy-4-[(3-oxo-6-hydroxy-1-benzofuran-2-yl}dene)-methyl]-benzene-1-oxide, 2-hydroxy-5-[(3-oxo-6-hydroxy-1-benzofuran-2-yli dene)-methyl]-benzene-1-oxide, or 3-oxo-2-[(3,4-dihydroxy-phen-1-yl)-methyli dene]-1-benzofuran-6-oxide; synhexyl anion: 6,6,9-trimethyl-3-hexyl-7,8,9,10-tetrahydro-6H-benzo [c]chromene-1-oxide; syringaldehyde anion: 2,6-dimethoxy-4-formyl-benzene-1-oxide; taxodi one anion: (4b S,8aS)-3,9-dioxo-4b,8,8-trimethyl-2-(prop-2-yl)-5,6,7,8 a-tetrahydro-phenanthrene-4-oxide; tectorigenin anion: 4-oxo-6-methoxy-5-hydroxy-3-(4-hydroxyphen-1-yl)-4H-chromen-7-oxide, 4-(4-oxo-6-methoxy-5,7-dihydroxy-4H-chromen-3-yl)-benzene-1-oxide, or 4-oxo-6-methoxy-7-hydroxy-3-(4-hydroxy-phen-1-yl)-4H-chromen-5-oxide; tetrahydrocannabinol anion: (6aR,10aR)-6,6,9-trimethyl-3-pentyl-6a,7,8,10a-tetrahydro-6H-benzo [c]chromene-1-oxide; delta8-tetrahydrocannabinol anion: (6aR,10aR)-6,6,9-trimethyl-3-pentyl-6a,7,10,10a-tetrahydro-6H-benzo [c]chromene-1-oxide; tetrahydrocannabiorcol anion: (6aR,10aR)-3,6,6,9-tetramethyl-6a,7,8,10a-tetrahydro-6H-benzo [c]chromene-1-oxide; tetrahydrocannabivarin anion: (6aR,10aR)-6,6,9-trimethyl-3-propyl-6a,7,8,10a-tetrahydro-6H-benzo[c]chromene-1-oxide; tetrahydrocannabinol-C4 anion: (6aR,10aR)-6,6,9-trimethyl-3-butyl-6a,7,8,10a-tetrahydro-6H-benzo [c]chromene-1-oxide; tetrahydrocannabiphorol anion: (6aR, 10aR)-6,6,9-trimethyl-3-heptyl-6a,7,8,10a-tetrahydro-6H-benzo [c]chromene-1-oxide; beta-thuj aplicin anion: 7-oxo-3-(prop-2-yl)-cycl ohepta-1,3,5-triene-1-oxide; alpha-thuj aplicin anion: 7-oxo-2-(prop-2-yl)-cyclohepta-1,3,5-triene-1-oxide; gamma-thujaplicin anion: 7-oxo-4-(prop-2-yl)-cycl ohepta-1,3,5-triene-1-oxide; thymol anion: 5-methyl-2-(prop-2-yl)-benzene-1-oxide; tioclomarol anion: 2-oxo-3-[3-hydroxy-3-(4-chloro-phen-1-yl)-1-(5-chl oro-thi ophen-2-yl)-prop-1-yl]-2H-chromene-4-oxide; alpha-tocopherol anion: (2R)-2,5,7,8-tetramethyl-2-[(4R,8R)-4,8,12-trimethyl-tri decyl]-3,4-dihydrochromen-6-oxide; beta-tocopherol anion: (2R)-2,5,8-trimethyl-2-[(4R,8R)-4,8,12-trimethyl-tri decyl]-3,4-dihydrochromen-6-oxide; gamma-tocopherol anion: (2R)-2,7,8-trimethyl-2-[(4R,8R)-4,8,12-trimethyl-tri decyl]-3,4-dihydrochromen-6-oxide; delta-tocopherol anion: (2R)-2,8-dimethyl-2-[(4R,8R)-4,8,12-trimethyl-tri decyl]-3,4-dihydrochromen-6-oxide; alpha-tocotrienol anion: (2R)-2,5,7,8-tetramethyl-2-[(3E,7E)-4,8,12-trimethyl-tri deca-3,7,11-tri ene-1-yl]-3,4-dihydrochromen-6-oxide; beta-tocotrienol anion: (2R)-2,5,8-trimethyl-2-[(3E,7E)-4,8,12-trimethyl-tri deca-3,7,11-triene-1-yl]-3,4-dihydrochromen-6-oxide; tolcapone anion: 6-hydroxy-4-[(4-methyl-phen-1-yl)-carbonyl]-2-nitro-benzene-1-oxide or 2-hydroxy-5-[(4-methyl-phen-1-yl)-carbonyl]-3-nitro-benzene-1-oxide; tyrosol anion: 4-(2-hydroxy-eth-1-yl)-benzene-1-oxide; uliginosin A anion: 3-oxo-5-hydroxy-6,6-dimethyl-2-(2-methyl-1-oxo-prop-1-yl)-4-[2, 4,6-trihydroxy-3-(3-methyl-but-2-en-1-yl)-5-(1-oxo-2-methyl-prop-1-yl)-phen-1-yl]-methyl-cyclohexa-1,4-diene-1-oxide, 3,5-dihydroxy-4-(3-methyl-but-2-en-1-yl)-6-(1-oxo-2-methyl-prop-1-yl)-2-[3-oxo-1,5-dihydroxy-6,6-dimethyl-4-(2-methyl-1-oxo-prop-1-yl)-cycl ohexa-1,4-dien-2-yl]-methyl-benzene-1-oxide, 3,5-dihydroxy-6-(3-methyl-but-2-en-1-yl)-4-(1-oxo-2-methyl-prop-1-yl)-2-[3-oxo-1,5-dihydroxy-6,6-dimethyl-4-(2-methyl-1-oxo-prop-1-yl)-cycl ohexa-1,4-dien-2-yl]-methyl-benzene-1-oxide, 3,5-dihydroxy-6-(3-methyl-but-2-en-1-yl)-2-(1-oxo-2-methyl-prop-1-yl)-4-[3-oxo-1,5-dihydroxy-6,6-dimethyl-4-(2-methyl-1-oxo-prop-1-yl)-cycl ohexa-1,4-dien-2-yl]-methyl-benzene-1-oxide, or 3-oxo-5-hydroxy-6,6-dimethyl-4-(2-methyl-1-oxo-prop-1-yl)-2-[2,4,6-trihydroxy-3-(3-methyl-but-2-en-1-yl)-5-(1-oxo-2-methyl-prop-1-yl)-phen-1-yl]-methyl-cyclohexa-1,4-diene-1-oxide; uliginosin B anion: 3-oxo-5-hydroxy-6,6-dimethyl-2-(2-methyl-1-oxo-prop-1-yl)-4-[5,7-dihydroxy-2,2-dimethyl-8-(2-methyl-1-oxo-prop-1-yl)-chromen-6-yl]-methyl 1-cy cl ohexa-1,4- dien-1-oxide, 7-hydroxy-2,2-dimethyl-8-(1-oxo-2-methyl-prop-1-yl)-6-[3-oxo-1,5-dihydroxy-6,6-dimethyl-4-(2-methyl-1-oxo-prop-1-yl)-cycl ohexa-1,4-dien-2-yl]-methyl 1-chromene-5-oxide, 5-hydroxy-2,2-dimethyl-8-(1-oxo-2-methyl-prop-1-yl)-6-[3-oxo-1,5-dihydroxy-6,6-dimethyl-4-(2-methyl-1-oxo-prop-1-yl)-cycl ohexa-1,4-dien-2-yl]-methyl 1-chromene-7-oxide, or 3-oxo-5-hydroxy-6,6-dimethyl-4-(2-methyl-1-oxo-prop-1-yl)-2-[5,7-dihydroxy-2,2-dimethyl-8-(2-methyl-1-oxo-prop-1-yl)-chromen-6-yl]-methyl 1-cycl ohexa-1,4-dien-1-oxide; umbelliferone anion: 2-oxo-2H-chromene-7-oxide; vanillin anion: 4-formyl-2-methoxy-benzene-1-oxide; vanillyl alcohol anion: 4-(hydroxymethyl)-2-methoxy-benzene-1-oxide; homovanillyl alcohol anion: 4-(2-hydroxy-eth-1-yl)-2-methoxy-benzene-1-oxide; violacein anion: 345-oxo-4-(2-oxo-1,3-dihydro-2H-indo1-3-ylidene)-4,5-dihydro-1H-pyrrol-2-yl]-1H-indo1-5-oxide; viridicatin anion: 2-oxo-4-phenyl-1H-quinolin-3-oxide; xanthoxylin anion: 3,5-dimethoxy-2-(1-oxo-eth-1-yl)-benzene-1-oxide; xibornol anion: 4,5-dimethyl-241,7,7-trimethyl-2-bicyclo[2.2.1]heptanyl]-benzene-1-oxide; zearalenone anion: (12E,4S)-2,8-dioxo-16-hydroxy-4-methyl-3-oxa-bicyclo[12.4.0]octadeca-12,14(15),16,18-tetraene-18-oxide or (12E,4S)-2,8-dioxo-18-hydroxy-4-methyl-3-oxa-bicyclo[12.4.0]octadeca-12,14(15),16,18-tetraene-16-oxide; zeranol anion: (4S,8R)-2-oxo-8,16-dihydroxy-4-methyl-3-oxa-bicyclo[12.4.0]octadeca-14(15),16,18-triene-18-oxide or (4S,8R)-2-oxo-8,18-dihydroxy-4-methyl-3-oxa-bicyclo[12.4.0]octadeca-14(15),16,18-triene-16-oxide; taleranol anion: (4S,8S)-2-oxo-8,16-dihydroxy-4-methyl-3-oxa-bicyclo[12.4.0]octadeca-14(15),16,18-triene-18-oxide or (4S,8S)-2-oxo-8,18-dihydroxy-4-methyl-3-oxa-bicyclo[12.4.0]octadeca-14(15),16,18-triene-16-oxide; alpha-zearalenol anion: (12E,4S,8R)-2-oxo-8,16-dihydroxy-4-methyl-3-oxa-bicyclo[12.4.0]octadeca-12,14(15),16,18-tetraene-18-oxide or (12E,4S,8R)-2-oxo-8,18-dihydroxy-4-methyl-3-oxa-bicyclo[12.4.0]octadeca-12,14(15),16,18-tetraene-16-oxide; beta-zearalenol anion: (12E,4S,8S)-2-oxo-8,16-dihydroxy-4-methyl-3-oxa-bicyclo[12.4.0]octadeca-12,14(15),16,18-tetraene-18-oxide or (12E,4S,8S)-2-oxo-8,18-dihydroxy-4-methyl-3-oxa-bicyclo[12.4.0]octadeca-12,14(15),16,18-tetraene-16-oxide; zingerone anion: 2-methoxy-4-(3-oxo-but-1-yl)-benzene-1-oxide; psiguadial A anion: (1S,9S,10R,11R,12R,14R,17S)-4,6-diformyl-5-hydroxy-10,13,13,17-tetramethyl-9-phenyl-2-oxa-pentacyclo[8.7.2.0$^{1,11}$.0$^{3,8}$.0$^{12,14}$]nonadeca-3(4),5,7-triene-7-oxide or (1S,9S,10R,11R,12R,14R,17S)-4,6-diformyl-7-hydroxy-10,13,13,17-tetramethyl-9-phenyl-2-oxa-pentacyclo[8.7.2.0$^{1,11}$.0$^{3,8}$.0$^{12,14}$]nonadeca-3(4),5,7-triene-5-oxide; psiguadial B anion: (1S,9R,10R,13S,14R,17S)-4,6-diformyl-5-hydroxy-13,16,16-trimethyl-9-phenyl-2-oxa-pentacyclo[11.6.1.0$^{1,11}$.0$^{3,8}$.0$^{14,17}$]icosa-3(4),5,7-triene-7-oxide or (1S,9R,10R,13S,14R,17S)-4,6-diformyl-7-hydroxy-13,16,16-trimethyl-9-phenyl-2-oxa-pentacyclo[11.6.1.0$^{1,10}$.0$^{3,8}$.0$^{14,17}$]icosa-3(4),5,7-triene-5-oxide; psiguadial C anion: (1S,9R,10R,12R,13R,18R,20R)-4,6-diformyl-5-hydroxy-10,14,19,19-tetramethyl-9-phenyl-2,13-dioxa-pentacyclo[8.10.0.0$^{3,8}$.0$^{12,14}$.0$^{18,20}$]icosa-3(4),5,7-triene-7-oxide or (1S,9R,10R,12R,13R,18R,20R)-4,6-diformyl-7-hydroxy-10,14,19,19-tetramethyl-9-phenyl-2,13-dioxa-pentacyclo[8.10.0.0$^{3,8}$.0$^{12,14}$.0$^{18,20}$]icosa-3($_4$) 5,7-triene-5-oxide; psiguadial D anion: (1S,9R,10R,13E,17S,19S)-4,6-diformyl-5-hydroxy-10,14,18,18-tetramethyl-9-phenyl-2-oxa-tetracyclo[8.10.0.0$^{3,8}$.0$^{17,19}$]nonadeca-3(4),5,7,13-tetraene-7-oxide or (1S,9R,10R,13E,17S,19S)-4,6-diformyl-7-hydroxy-10,14,18,18-tetramethyl-9-phenyl-2-oxa-tetracyclo[8.10.0.0$^{3,8}$.0$^{17,19}$]nonadeca-3(4),5,7,13-tetraene-5-oxide; cavicularin anion: 6-hydroxy-3,5-(5-hydroxybibenzyl-2,4'-diyl-4'-oxy)-9,10-dihydro-phenanthrene-1-oxide, 6,O'-(2,6-dihydroxy-9,10-dihydro-phenanthren-3,5-diyl)-4'-oxybibenzyl-3-oxide, or 2-hydroxy-3,5-(5-hydroxybibenzyl-2,4'-diyl-4'-oxy)-9,10-dihydro-phenanthrene-6-oxide; and raspberry ketone anion: 4-(3-oxo-but-1-yl)-benzene-1-oxide.

The anions set forth in the preceding paragraph can be produced by incubating their conjugate acids with a strong Brønsted base in an alcohol, for example, as described in U.S. Pat. No. 10,555,914 B1. The conjugate acids can be readily identified by looking up the common names annotated above in THE MERCK INDEX. The utility of each anion, for example, parallels the utility of its conjugate acid as described in THE MERCK INDEX. Some of the conjugate acids lack a monograph in THE MERCK INDEX, and each conjugate acid that lacks a monograph in THE MERCK INDEX is related to the conjugate acid that immediately precedes it in the preceding paragraph such that one of ordinary skill may readily identify methods to produce and use every anion of the preceding paragraph by simply reviewing this patent document and consulting THE MERCK INDEX.

Various aspects of this patent document relate to a method to produce a composition according to any one of the embodiments described in this patent document, comprising: combining a molecule, a strong Brønsted base, and an initial alcohol to produce a first composition that comprises an anion, wherein the anion is dissolved in the initial alcohol; providing a second composition that comprises a solvent; and combining the first composition and the second composition to dissolve the anion in the solvent. In some embodiments, the method comprises separating the anion from the initial alcohol and the solvent to produce a solid phase that comprises a salt. "Brønsted base" refers to a proton acceptor.

Exemplification. Examples 1-8 set forth specific embodiments of this disclosure, and examples 1-8 do not limit the scope of the disclosure or any claim that matures from this patent document.

Example 1

Eugenol Anion

Eugenol, which has a structure according to formula I, was deprotonated in ethanolic potassium hydroxide to produce the eugenol anion 2-methoxy-4-(prop-2-en-1-yl)-benzene-1-oxide. The mixture was combined with glycerol at a ratio of about 1:3 by mass. The resultant combination was administered orally to humans.

Example 2

Cannabigerol Anion

Cannabigerol, which has a structure according to formula I, was deprotonated in ethanolic potassium hydroxide to produce the cannabigerol anion 2-geranyl-3-hydroxy-5-pentylbenzene-1-oxide. The mixture was combined with glycerol at ratios of about 1:2 and 1:3 by mass. Similarly-prepared mixtures were combined with water to produce beverages containing about 10 milligrams of the cannabigerol anion per 355 milliliter serving, which is greater than the solubility of molecular cannabigerol in water. Beverage formulations were also prepared at concentrations greater than 400 milligrams per liter. The oral administration of both the glycerol and beverage formulations to humans resulted in moderate, perceptible sedation in less than 5 minutes, which suggests that the reprotonated cannabigerol anion was rapidly absorbed through the epithelial lining of the mouth and throat. The mild sedation improved sleep quality both in individuals with no diagnosed sleep conditions and in an individual who presented with chronic insomnia. Formulations of the cannabigerol anion also displayed anxiolytic activity in some individuals with an onset time of less than 5 minutes.

Example 3

Quercetin Anions

Quercetin, which has a structure according to formulas III and XIII, was deprotonated in ethanolic potassium hydroxide to produce the quercetin anions 4-oxo-3,7-dihydroxy-2-(3,4-dihydroxy-phen-1-yl)-4H-chromene-5-oxide, 4-oxo-3,5-dihydroxy-2-(3,4-dihydroxy-phen-1-yl)-4H-chromene-7-oxide, 2-hydroxy-4-(4-oxo-3,5,7-trihydroxy-4H-chromene-2-yl)-benzene-1-oxide, 2-hydroxy-5-(4-oxo-3,5,7-trihydroxy-4H-chromene-2-yl)-benzene-1-oxide, and 4-oxo-5,7-dihydroxy-2-(3,4-dihydroxy-phen-1-yl)-4H-chromene-3-oxide. The mixture was combined with glycerol at a ratio of about 1:3 by mass and then administered to humans.

Example 4

Cannabidiol Anion

Cannabidiol, which has a structure according to formula IV, was deprotonated in ethanolic potassium hydroxide to produce the cannabidiol anion 3-hydroxy-2-[(1R,6R)-6-(prop-1-en-2-yl)-3-methyl-cyclohex-2-en-1-yl]-5-pentyl-benzene-1-oxide at a concentration of about 50 grams per liter, which is greater than literature values for the solubility of molecular cannabidiol in ethanol. The mixture was combined with glycerol at ratios of about 1:2 and 1:3 by mass at concentrations ranging from 1 to 25 grams per liter, which is greater than the solubility of molecular cannabidiol in glycerol. The cannabidiol anion was also dissolved in other sugar alcohols including a solution comprising about 80 percent sorbitol and about 20 percent ethanol by mass at a concentration of approximately 40 grams cannabidiol anion per liter. Other mixtures were combined with water to produce beverages containing about 10 milligrams of the cannabidiol anion per 355 milliliter serving, which is greater than the solubility of molecular cannabidiol in water. Beverage formulations were also prepared at concentrations greater than 400 milligrams per liter.

The oral administration of both the glycerol formulations and the beverage formulations to humans resulted in perceptible analgesic and anxiolytic effects in less than 5 minutes, which suggests that the reprotonated cannabidiol anion was rapidly absorbed through the epithelial lining of the mouth and throat. The glycerol formulation was administered to an individual who was unable to fill her hydroxychloroquine prescription to treat rheumatoid arthritis during the COVID-19 pandemic, for example, and she reported that the formulation was more effective at treating her arthritis symptoms than hydroxychloroquine.

The glycerol formulation was administered to an epileptic dog during multiple active seizures, and the formulation consistently and instantaneously arrested the seizures at a dose of about 0.5-1.0 milligrams per kilogram bodyweight. The FDA- and EMA-approved cannabidiol pharmaceutical EPIDIOLEX® is administered to humans at 5-20 milligrams per kilogram bodyweight per day to treat epilepsy, but EPIDIOLEX® is not known to arrest active seizures. The ability of the cannabidiol anion to arrest active seizures at one-tenth of the dose of EPIDIOLEX® suggests that the reprotonated cannabidiol anion was rapidly absorbed through the epithelial lining of the mouth and throat to avoid cytochrome P450-mediated oxidation in the liver.

The glycerol formulation was administered topically to humans, and the formulation changed color from purple, which is indicative of the cannabidiol anion, to colorless, which is indicative of molecular cannabidiol.

Example 5

Resveratrol Anions

Resveratrol, which has a structure according to formula VII, was deprotonated in ethanolic potassium hydroxide to produce the resveratrol anions 3-hydroxy-5-[(E)-2-(4-hydroxyphen-1-yl)-ethen-1-yl]-benzene-1-oxide and 4-[(E)-2-(3,5-hydroxy-phen-1-yl)-ethen-1-yl]-benzene-1-oxide. The mixture was combined with glycerol at ratios of about 1:2 and 1:3 by mass and then administered orally to a human.

Example 6

Curcumin Anion

Curcumin, which has a structure according to formula X, was deprotonated in ethanolic potassium hydroxide to produce the curcumin anion 2-methoxy-4-[7-(4-hydroxy-3-methoxy-phen-1-yl)-3,5-dioxo-hepta-1,6-diene-1-yl]-benzene-1-oxide at concentrations exceeding 100 grams per liter, which is more than 10 times greater than literature values for the solubility of curcumin in ethanol. The mixture was combined with glycerol at ratios of about 1:2 and 1:3 at a concentration of about 25 grams per liter, which is more than 10 times greater than literature values for the solubility of curcumin in glycerol. Similarly-prepared mixtures were combined with water to produce beverages containing about 100 milligrams of the curcumin anion per 355 milliliter serving, which is more than 10 times greater than literature values for the solubility of curcumin in water. Beverage formulations were also prepared at concentrations greater than 400 milligrams per liter.

The oral administration of both the glycerol formulations and the beverage formulations to adult humans resulted in perceptible psychoactive effects in individuals who were naive to the curcumin anion within 5 minutes of consumption, which suggests that the reprotonated curcumin anion was rapidly absorbed through the epithelial lining of the mouth and throat.

Example 7

Tetrahydrocannabinol Anion

Tetrahydrocannabinol, which has a structure according to formulas III and XII, was deprotonated in ethanolic potassium hydroxide to produce the tetrahydrocannabinol anion (6aR,10aR)-6,6,9-trimethyl-3-pentyl-6a,7,8,10a-tetrahydro-6H-benzo[c]chromene-1-oxide. The mixture was combined with glycerol at a ratio of about 1:3 by mass at a concentration of about 1 gram per liter. Similarly-prepared mixtures were also combined with water to formulate beverages containing the tetrahydrocannabinol anion at concentrations exceeding 100 milligrams per liter, which is more than 10 times greater than the solubility of molecular tetrahydrocannabinol in water.

The standard oral dose of tetrahydrocannabinol is 10 milligrams, which produces psychoactive effects in most humans. The psychoactive effects of tetrahydrocannabinol are mediated by its bioactive metabolite 11-hydroxy tetrahydrocannabinol, which is produced by cytochrome P450 in the lungs and liver. A 10 milligram dose of the tetrahydrocannabinol anion dissolved in glycerol did not produce any perceptible psychoactive effect, but beverage formulations displayed psychoactive effects within 30 minutes. These results suggest that (1) glycerol formulations were predominantly absorbed through the epithelial lining of the mouth and throat, which bypassed the liver and avoided the conversion of tetrahydrocannabinol into 11-hydroxy tetrahydrocannabinol by cytochrome P450, whereas (2) a significant portion of the beverage formulations was absorbed in the stomach, which allowed the conversion of tetrahydrocannabinol into 11-hydroxy tetrahydrocannabinol on a timeframe consistent with liver-mediated cytochrome P450 oxidation.

Example 8

Epigallocatechin Gallate Anions

Epigallocatechin gallate, which has a structure according to formulas III, XIII, and XVI, was deprotonated in ethanolic potassium hydroxide to produce the epigallocatechin gallate anions 2,6-dihydroxy-4-({[(2R,3R)-5,7-dihydroxy-2-(3,4,5-trihydroxy-phen-1-yl)-3,4-dihydro-2H-chromen-3-yl]-oxy}-carbonyl)-benzene-1-oxide, (2R,3R)-7-hydroxy-2-(3,4,5-trihydroxy-phen-1-yl)-3-{[(3,4,5-trihydroxy-phen-1-yl)-carbonyl]-oxy}-3,4-dihydro-2H-chromene-5-oxide, (2R, 3R)-5-hydroxy-2-(3,4,5-trihydroxy-phen-1-yl)-3-{[(3,4,5-trihydroxy-phen-1-yl)-carbonyl]-oxy}-3,4-dihydro-2H-chromene-7-oxide, 2,3-dihydroxy-5-[(2R,3R)-5,7-dihydroxy-3-{[(3,4,5-trihydroxy-phen-1-yl)-carbonyl]-oxy}-3,4-dihydro-2H-chromen-2-yl]-benzene-1-oxide, 2,6-dihydroxy-4-[(2R,3R)-5,7-dihydroxy-3-{[(3,4,5-trihydroxy-phen-1-yl)-carbonyl]-oxy}-3,4-dihydro-2H-chromen-2-yl]-benzene-1-oxide, and 2,3-dihydroxy-5-({[(2R,3R)-5,7-dihydroxy-2-(3,4,5-trihydroxy-phen-1-yl)-3,4-dihydro-2H-chromen-3-yl]-oxy}-carbonyl)-benzene-1-oxide. The mixture was combined with glycerol at a ratio of about 1:3 by mass and then administered orally to humans.

What is claimed is:

1. A composition comprising a liquid phase that comprises a potassium cation, an anion and a solvent, and further comprises ethanol, wherein:
the solvent is at a concentration of at least 50 percent by mass;
the solvent is propane-1,2,3-triol;
the anion is dissolved in the solvent;
the anion has a net charge of −1;
the anion has a conjugate acid that is a molecule;
the molecule has a net charge of zero;
the molecule has a solubility in water that is less than 10 grams per liter at a pH of 7;
the molecule comprises a hydroxyl group that comprises an oxygen atom that is covalently bound to a carbon atom of an aromatic ring of the molecule by a single bond;

the anion comprises exactly one oxide group, and the oxide group comprises an oxygen atom that is covalently bound to a carbon atom of an aromatic ring of the anion by a single bond;
the oxygen atom of the hydroxyl group of the molecule has a connectivity to other heavy atoms of the molecule;
the oxygen atom of the oxide group of the anion has a connectivity to other heavy atoms of the anion; and
the connectivity of the oxygen atom of the hydroxyl group of the molecule to other heavy atoms of the molecule is identical to the connectivity of the oxygen atom of the oxide group of the anion to other heavy atoms of the anion;
the anion has a general formula I;

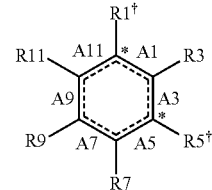

each skeletal atom of general formula I is a carbon atom;
the dotted lines represent aromaticity;
R1† is oxide; R3 is 6-(prop-1-en-2-yl)-3-methyl-cyclohex-2-en-1-yl; R5t is hydroxy; R7 is H; R11 is H; and
R9 is selected from an unsubstituted C3-C10 cycloalkyl; and a substituted or unsubstituted, straight or branched C1-12 alkyl; wherein substitution refers to at least one of:
(i) the substitution of two hydrogen atoms with a double bond;
(ii) the substitution of a hydrogen atom with an unsubstituted straight C1-C12 alkyl; and
(iii) the substitution of two hydrogen atoms with methylene or an unsubstituted, straight C1-C12 alkyl such that the substitution of the two hydrogen atoms forms a cycle that consists of 3 to 14 atoms; and
R9 is selected such that the anion comprises (i) at least 6 and no greater than 45 carbon atoms, (ii) at least 5 and no greater than 60 hydrogen atoms, and (iii) at least 1 and no greater than 12 oxygen atoms.

2. The composition of claim 1, comprising water.

3. The composition of claim 1, comprising the cation and the anion at a molar ratio of at least 1:1 and no greater than 5:4.

4. The composition of claim 1, comprising a concentration of the anion that is dissolved in the solvent, wherein the molecule has a solubility in the liquid phase at a neutral pH that is less than the concentration of the anion that is dissolved in the solvent.

5. The composition of claim 1, comprising the molecule and the anion at a molar ratio of at least 1:1,000,000 and less than 10:1.

6. The composition of claim 1, comprising the anion at a concentration of at least 1 gram per liter.

7. The composition of claim 1, wherein R9 is selected from methyl; ethyl; propyl; butyl; pentyl; hexyl; heptyl; ethenyl; prop-1-enyl; propen-2-yl; isoprenyl; geranyl; and a methyl, ethyl, propyl, butyl, pentyl, hexyl or heptyl that is substituted with 1, 2, or 3 groups selected from methyl, ethyl, and propyl.

8. The composition of claim 1, wherein the anion is selected from
- 3-hydroxy-2-[(1R,6R)-6-(prop-1-en-2-yl)-3-methyl-cyclohex-2-en-1-yl]-5-pentyl-benzene-1-oxide;
- 3-hydroxy-2-[(1R,6R)-6-(prop-1-en-2-yl)-3-methyl-cyclohex-2-en-1-yl]-5-propyl-benzene-1-oxide;
- 3-hydroxy-2-[(1R,6R)-6-(prop-1-en-2-yl)-3-methyl-cyclohex-2-en-1-yl]-5-heptyl-benzene-1-oxide; and
- 3-hydroxy-2-[(1R,6R)-6-(prop-1-en-2-yl)-3-methyl-cyclohex-2-en-1-yl]-5-(2-methyl-octan-2-yl)-benzene-1-oxide.

9. The composition of claim 1, wherein the anion is 3-hydroxy-2-[(1R,6R)-6-(prop-1-en-2-yl)-3-methyl-cyclohex-2-en-1-yl]-5-pentyl-benzene-1-oxide.

10. A method to produce a composition according to claim 1, comprising:
- combining the molecule, a strong Brønsted base comprising potassium, and an initial alcohol comprising ethanol to produce a first composition that comprises the anion, wherein the anion is dissolved in the initial alcohol;
- providing a second composition that comprises propane-1,2,3-triol as solvent; and
- combining the first composition and the second composition to dissolve the anion in the solvent and produce the composition of claim 1.

* * * * *